United States Patent [19]
Khwaja et al.

[11] Patent Number: 6,039,950
[45] Date of Patent: Mar. 21, 2000

[54] PHARMACEUTICAL GRADE SAW PALMETTO

[75] Inventors: Tasneem A. Khwaja, Corona Del Mar; Elliot P. Friedman, Montecito, both of Calif.

[73] Assignees: University of Southern California, Los Angeles; Pharmaprint Inc., Irvine, both of Calif.

[21] Appl. No.: 08/956,601

[22] Filed: Oct. 23, 1997

Related U.S. Application Data

[63] Continuation-in-part of application No. 08/838,198, Apr. 15, 1997, abandoned, which is a continuation-in-part of application No. 08/632,273, Apr. 15, 1996, which is a continuation-in-part of application No. 08/421,993, Apr. 14, 1995, abandoned, which is a continuation-in-part of application No. 08/774,550, Feb. 4, 1997.

[51] Int. Cl.[7] .................................................. A61K 35/78
[52] U.S. Cl. ........................................................ 424/195.1
[58] Field of Search ........................ 424/195.1; 514/869, 514/906

[56] References Cited

U.S. PATENT DOCUMENTS 5,284,873   2/1994   Salinero-Rodero et al. ........... 514/558

FOREIGN PATENT DOCUMENTS 4-275225   9/1992   Japan .

OTHER PUBLICATIONS

Colegate S. Bioactive Natural Products, CRC Press, Boca Raton FL, pp. 3, 200–201, 1993.

Rossi G. Biological Testing. Remington's Pharmaceutical Sciences, Philadelphia College of Pharmacy and Science, Chapter 31 pp. 520–531, 1980.

Khwaja T. Recent Studies on the Anticancer Activities of Mistletoe and Its Alkaloids. Oncology 43(1)42–50, 1986.

Niederprüm, H–J. et al., "Inhibition of Steroid 5α–Reductase Activity by Aliphatic Fatty Acids," *Annals N.Y. Acad. Sci.*, vol. 768, pp. 227–230 (Sep. 30, 1995).

Cristoni A., Chemical and Pharmacological Study on Hypercritical $CO_2$ Extracts of Serenoa repens Fruits, Fitoterapia 68(4)355–358, Apr. 1997.

DeSwaef S. Supercritical Fluid Chromatography of Free Fatty Acids and Ethyl Esters in Ethanolic Extracts of Sabal serrulata, 7(5)223–7, May 1996.

*Primary Examiner*—Ralph Gitomer
*Attorney, Agent, or Firm*—Lyon & Lyon LLP

[57] ABSTRACT

The present invention relates generally to saw palmetto materials and methods for making such materials in medicinally useful and pharmaceutically acceptable forms. More particularly, the present invention relates to the use of compositional and activity fingerprints in the processing of saw palmetto materials to produce drugs which qualify as pharmaceutical grade compositions which are suitable for use in clinical or veterinary settings to treat and/or ameliorate diseases, disorders or conditions.

1 Claim, 8 Drawing Sheets

PHARMACEUTICAL GRADE SAW PALMETTO

This is a continuation-in-part of U.S. Ser. No. 08/838,198, filed on Apr. 15, 1997, now abandoned, which is a continuation-in-part of co-pending U.S. Ser. No. 08/632,273, filed on Apr. 15, 1996, which is a continuation-in-part of U.S. Ser. No. 08/421,993, filed on Apr. 14, 1995 abandoned in favor of U.S. Ser. No. 08/774,550, filed Feb. 4, 1997.

1. FIELD OF THE INVENTION

The present invention relates generally to botanical materials and methods for transforming such materials into medicinally useful and pharmaceutically acceptable forms. More particularly, the present invention relates to the use of compositional and activity fingerprints in the processing of saw palmetto to produce botanical drugs which qualify as pharmaceutical grade compositions which are suitable for use in clinical settings to treat and/or ameliorate diseases, disorders and/or conditions.

2. BACKGROUND OF THE INVENTION

Pharmaceutical manufacturing is based on control over the composition and bioactivity for each manufactured batch. This standardization and control provides reproducible material in the predictable and consistent treatment of patients. Herbal medicines, produced from botanical materials, have presented a unique problem for manufacturers desiring the control, reproducibility, and standardization that are required of pharmaceuticals. This problem is primarily due to the plurality of components contained in an herbal medicine and the large variation in composition and potency due to the growing, harvesting and processing conditions of raw materials.

Plants have been, and continue to be, the source of a wide variety of medicinal compounds. For centuries, various forms of botanically derived materials have been used to treat countless different ailments. The botanical materials have typically been in the form of powders made from one or more plants or plant parts or extracts derived from whole plants or selected plant parts. These powders and extracts are, for the most part, complex mixtures of both biologically active and biologically inactive compounds.

Although plant powders and extracts have been used widely for medicinal purposes, there are a number of problems associated with the use of such medicaments. For example, the complex chemical nature of the botanical materials makes it difficult to use the botanical materials in any type of controlled and predictable manner. The potential variations in the chemical composition of different batches of material obtained from different plant harvests makes such materials unsuitable for use in clinical situations.

On a positive note, the complex groupings of bioactive components typically found in botanical materials presents the potential for synergistic or additive bioactivity profiles. However, these potential increases in medicinal effectiveness are not predictable due to the unknown nature of these complex materials.

The above problems associated with the inherent chemical complexity of botanical medicaments has resulted in a great deal of effort being directed to the separation and isolation of the biologically active components from numerous medicinally important botanical materials. This area of endeavor has expanded rapidly in conjunction with the many improvements in chemical separation and analysis technology. Once isolated and purified, the various active components are used in clinical settings to establish the medicinal effectiveness of a specific component. Separation and purification of individual components from botanical materials is the cornerstone of this type of drug development procedure. Once purified, the suspected active component is typically mixed with a pharmaceutically acceptable carrier and subjected to further studies in laboratory animals and eventual clinical trials in humans. Upon proof of clinical efficacy, these types of drugs are considered to be pharmaceutical grade because they contain a single, or at most a small number of, well-characterized compounds which are present in known quantities.

Pharmaceutical grade drugs are advantageous in that they allow careful tracking of the effects of individual compounds in treatment protocols. Further, the dosage of the drug can be carefully controlled to provide relatively predictable medicinal action. A disadvantage of the relative purity of such pharmaceutical grade drugs is that the potential for complex and synergistic biological activity provided by naturally occurring plant materials is reduced because of the isolation of the drug from its natural environment. The study of isolated products may also represent artifacts produced by breakdown of sensitive biological/botanical complexes. The potential benefit provided by such synergistic activity is believed by many industry experts to be outweighed by the clinical risks associated with the use of complex plant materials which are not well characterized or controlled in a clinical setting.

Although isolation and purification of single compounds from plant materials has been a popular form of drug research and development, there has also been interest in studying complex botanical extracts to characterize their medicinal qualities. Many complex plant materials and extracts exist which have potent, but relatively unpredictable, medicinal properties. These materials are, for the most part, useless in a clinical setting because of the inherent risks involved with treating patients with poorly characterized materials which have no established batch consistency and which may differ widely in composition. Accordingly, there is a need to provide methods for standardizing such complex botanical materials so that they may be used more effectively in clinical research and patient treatments.

2.1 Saw Palmetto

The Saw Palmetto is a small palm indigenous to the southern United States. In botanical preparations, the small brownish-colored berries have been used for many years to treat diseases of the bladder and the prostate. Extracts of the Saw Palmetto are prepared in variety of ways, typically, hexane extraction or supercritical carbon dioxide extraction. There are also lipidic extracts and saponifiable extracts that are commercially available from Madaus, S.A.

2.2 Clinical Use for Alleviation of the Symptoms of Benign Prostatic Hypertrophy In Europe, botanical materials represent nearly half of all prescriptions for benign prostatic hypertrophy (BPH) (Di Silverio et al., 1993, *Minerva Urol. Nefrol.* 45:143–9) (Di Silverio et al.). Some of the more common plant extracts, or phytotherapeutics, prescribed for BPH are obtained from: *Serenoa repens* (Saw Palmetto Berry), *Pygeum africanum* (Plum Bark), and *Cucurbita pepo* (Pumpkin Seed). By far the most widely used botanical material for the treatment of BPH is a lipid extract of Saw Palmetto berries. Saw Palmetto Berry extract (SPB-extract) is nontoxic and has demonstrated few or no adverse side effects in clinical trials. The most extensive clinical trials of SPB-extract were conducted in France. In these trials the SPB-extract Permixon was used. This extract has been commercially available since 1982. According to French scientists, Permixon is very safe, and there is little evidence of undesirable side effects. Today, Permixon and a variety of other products are available in over twenty countries throughout the world.

The mechanism of action of saw palmetto extracts (noted above) is not obvious; various investigators have presented evidence in support of, or in opposition to, several different mechanisms. Saw palmetto clearly does not behave the same as Finasteride (Proscar™), which is a demonstrated systemic 5α-reductase inhibitor. Since Finasteride blocks conversion of testosterone to dihydroxytestosterone (DHT) in the circulation, its effect can be measured in serum as a decrease in serum DHT levels. Several investigators have reported that this is not the case for the saw palmetto extract, Permixon. If the active component of Permixon is selectively concentrated in prostate tissue (and it should be noted that there are limited data at present that this is the case) then the mechanism of action for Permixon™ may still involve 5α-reductase inhibition of testosterone metabolism in the prostate, perhaps in specialized tissues (e.g., epithelial tissue or stroma). A key finding arguing against this is the report by Délos et al, that the vast majority (80%) of testosterone, when added to prostate cells, is converted to androstenedione by the enzyme 17β-hydroxysteroid dehydrogenase (17β-HSD), and only 2–5% is converted to DHT by the enzyme 5α-reductase. (Délos S, et al., 1995, *J Steroid Biochem Mol Biol* 55(3/4):375–383.)

Since saw palmetto extracts are multi-component mixtures, it may be reasonable to assume that their overall anti-prostatic activity will be multifocal, as suggested by Carilla and others. (Carilla E, et al. 1984, *J steroid Biochem* 20(1):521–523.) Anti-prostatic mechanisms of action, reviewed in studies below, involve: 5α-reductase inhibition, antiandrogenic, antiestrogenic, anti-inflammatory, antiedematous, immunostimulatory and smooth muscle relaxing activities.

Review Articles

Two comprehensive articles were published in French in 1993 by Eugene Neuzil (University of Bordeaux) and Henri Cousse (whose affiliation is Pierre Fabre Médicament, the manufacturer of Permixon™). One is entitled "The Saw Palmetto *Serenoa repens*; Botanical And Chemical Aspects" *Bull Soc Pharm Bordeaux* (France) 1993;132:121–141, and the other is "The Saw Palmetto Serenoa repens; Pharmacological Aspects, Current Therapeutic Uses" *Bull. Soc. Pharm. Bordeaux* (France) 1993;132:142–163.

The first article includes specific information on the discovery of the North-American palm tree and its botanical characteristics. *Serenoa repens* belongs to the sub-family of Coryphoideae, and to the tribe of Corypheae. The name of the genus Serenoa was suggested by Hooker in memory of Sereno Watson (1826–1892), an American botanist and the author of an authoritative book on the botany of California. The taxonomy of palms is confusing in the literature, and many names designate the same plant: *Serenoa repens* (Bartram) Small, *Corypha repens, Sabal levistona Feay, Sabal serrulata* Roemer and Schultes, and *Brahea serrulata* (Michaux) Wendl. Also related, but thought by some botanists to be different species, are: *S. serrulata* Hook., synonymous with *Diglossophyllum serrulatum* Wendl., and *S. arborescens* Sarg., synonymous with *Paurotis arborescens* O. F. Cook and also with *Acoelorraphe arborescens* Becc.

The saw palmetto *Serenoa repens* (Bartram) Small is a plant typical of the southeastern states of the United States, where it forms thick bushes, especially in coastal areas. The fruits are harvested when ripe, from September to November. They are shipped fresh or more or less dry for commercial distribution. To complicate matters, another dwarf palm, *Sabal palmetto* (Walter) Loddiges ex. J. A. & J. H. Schutes, lives in the regions where *S. repens* grows. The distinction between the two species is based on different physical characteristics of the plants and fruit. The review continues with a comprehensive presentation of the chemical compounds of the drupe of *S. repens*. J. B. Read (in 1879) reported that he observed three immiscible phases when the expressed liquid obtained from the fresh fruits settles: a volatile yellow essential oil, a brown lipidic oily phase and an aqueous yellowish phase with a sugary taste. In 1899, Sherman and Briggs, showed that the oil obtained from the pulp is very different from the one isolated from the seeds. The same authors noticed the presence of sugars and the absence of alkaloids. They provided the first analyses of the fatty acids present in the oily phase; a high proportion (37%) of these fatty acids are in the form of ethyl esters, and not triglycerides, which are present in the oil from the seeds. The ethyl esters do not appear to be artifacts from the storage of the drupes in alcohol.

In addition to the fatty acids and fatty acid esters, there is also a small percentage (2–3%) of long chain fatty acids (>C24). In addition to these fatty acid constituents, the berries of *S. repens* contain tannins, colorants, invert sugars, mannitol, and the phytosterols β-sitosterol, campesterol, stigmasterol and cycloartenol. The β-sitosterol is present in a relatively high concentration: 18.9 mg % as free β-sitosterol and 27.7 mg % as its glucoside.

Source documents for the more commonly used extraction techniques are cited (e.g., for: ethanol, acetone, carbon dioxide at the supercritical state, and hexane). Most of the remainder of this review paper is devoted to details of the chemical composition of the hexane extract, the basis of the pharmaceutical Permixon, which is widely prescribed in France, Italy and Spain, and is the product of the company employing one of the authors of this review. However, it includes a few details of the aqueous extract (which contains a polysaccharide acid with intense anti-inflammatory activity) and the alcoholic extract (which contains selected flavonoids, such as, rutin, isoquercitin, the 3-0-glucoside of campferol and the 7-0-rhamnoglucoside of apigenine).

The second review paper states that saw palmetto extracts exert their therapeutic effect by interfering with hormonal metabolism and by virtue of their anti-inflammatory properties. After giving anecdotal historical accounts of the utility of extracts of *S. repens* for various indications throughout the past 100 years, the review discusses animal experimentation that elucidates the relationship between androgens and the prostate gland in benign prostate hyperplasia (BPH), including evidence for the involvement of 5α-reductase. It proceeds to describe toxicological studies at Pierre Fabre Médicament indicating that the *S. repens* lipidic sterolic hexane extract (i.e., Permixon) is quite non-toxic: 10 ml/kg showed no adverse effects in rats or mice in acute tests. This lack of toxicity was confirmed in subacute and chronic studies. Tests for mutagenicity and chromosomal aberrations were also found to be negative. Pharmacokinetic studies showed absorption of saponified and non-saponified radiolabeled fractions to be slow (4 to 10 hours). The tritiated saponified fraction distributed to the digestive tract, bile, liver and kidneys, and elimination from the spleen and bone marrow is slow. In contrast, distribution of the tritiated non-saponified fraction is low, and its elimination is rapid.

The disposition of *S. repens* lipidic sterolic hexane extract from tablets, gelcaps and capsules was compared in the dog after radioactive labeling with tritium (internal studies, Pierre Fabre Médicament). The kinetics of the radioactive pool, measured in blood, in plasma, urine and feces, were followed for 120 hours after administration. No important differences were observed amongst the three dosage forms.

The remainder of this review article describes various animal studies using *S. repens* extracts, most of which are detailed in the sections below. Briefly, there are comments dealing with receptor interactions (androgen, estrogen, prolactin), 5α-reductase inhibition (*S. repens* extracts are good inhibitors of type 1 (epithelial) 5α-reductase, but in contrast to Finasteride, they are not selective inhibitors of type 2 (stromal) 5α-reductase), non-corticoid anti-inflammatory effects (carrageenan paw edema, reduction in capillary permeability caused by histamine), and the effects of *S. repens* extracts on cyclooxygenase and lipoxygenase pathways.

The review concludes by indicating that the symptoms of BPH are effectively treated by the use of the extracts of the saw palmetto *Serenoa repens*. The extracts of *Serenoa repens*, and especially the lipid/sterolic extract, have demonstrated clinical efficacy by virtue of their double pharmacological actions of antiandrogenic action (without side effects) and anti-inflammatory action (reducing the vesico-prostatic muscular tonus).

Mechanism of Action

This section reviews one or more mechanisms of action for the use of saw palmetto berry extracts in the treatment of benign prostatic hyperplasia (BPH). Discussed below are six papers involving 5α-reductase (both pro and con), four papers treating steroid receptor (androgen and estrogen) interactions, four papers on anti-inflammatory properties, and one each on immunomodulation and muscle relaxant mechanisms. Papers in each section are presented in reverse chronological order, by year.

5α-Reductase Mechanism of Action

Weisser H, et al. studied the "Effects of the *Sabal Serrulata* Extract IDS 89 and its Subfractions on 5α-reductase Activity in Human Benign Prostatic Hyperplasia" in *The Prostate* 1996;28:300–306.. Using epithelium and stroma prepared from human prostate, they found a dose-dependent and non-competitive inhibition of 5α-reductase in human prostate epithelium and stroma (39% and 38%, respectively) with IDS 89 (extract of *Sabal serrulata*). This inhibition is not caused by binding of IDS at the active center of 5α-reductase, but instead the binding is "elsewhere". They reported that the $IC_{50}$ for IDS 89 was 2.2 mg/ml (2200 µg/ml) in whole prostate homogenates, a very high concentration which could be influencing cell viability and/or membrane function independently of 5α-reductase activity.

Délos S. et al. used both Finasteride (Proscar™) and a lipid/sterol extract from *Serenoa repens* (LSESr). They found in all cultures, 80% of added testosterone was converted to androstenedione by the enzyme 17β-Hydroxysteriod dehydrogenase (17β-HSD). The amounts of testosterone converted to DHT by 5α-reductase, on the other hand, were small (2–5% in BPH cells). 5α-reductase type 1 is confined to epithelial cells, and type 2 occurs predominantly in stromal cells. DHT formation in epithelial cells (type 1) was inhibited more by 4-MA (a 5α-reductase inhibitor) than by Finasteride (Proscar™). Inhibition of DHT formation by the two agents in fibroblasts was equipotent ($IC_{50}$=50 and 30 nM, respectively).

LSESr inhibited the production of both DHT and androstenedione, suggesting it is an inhibitor of both 5α-reductase and 17β-hydroxysteroid dehydrogenase (17β-HSD). The data for DHT inhibition are summarized in Table 1. An inhibitory mechanism involving LSESr's lipid/sterol composition was invoked by the authors, who conclude that LSESr inhibits the 5α-reductase type 1 ($IC_{50}$=30 µg/ml) and possibly 17β-HSD of primary human prostate cells, while Finasteride preferentially inhibits 5α-reductase type 2.

TABLE 1

| | Inhibition of DHT | |
|---|---|---|
| $IC_{50}$ for DHT Inhibition by: | Epithelial cells (type 1) | Stroma (type 2) |
| 4-MA | 20 nM | 50 nM |
| Finasteride | 400 nM | 30 nM |
| LSESr | 30 µg/ml | 10 µg/ml |

In a related paper, Délos S, Iehlé C, Martin P M, and Raynaud J P studied the "Inhibition of the Activity of "Basic" 5α-Reductase (Type 1) Detected in DU 145 Cells and Expressed in Insect Cells" to characterize the type 1 isoform of the enzyme in terms of type of inhibition and $IC_{50}$ (Delos S. J. 1995 Steroid Biochem Mol. Biol 48:(3/4) 347–352). They were able to show that only Type 1 5α-reductase is expressed in these cells, and when used at recommended doses, LSESr inhibition was three-fold greater than that of Finasteride, as shown in Table 2. The LSESr inhibition of 5α-reductase is augmented by its lipid/sterol composition.

TABLE 2

| | Inhibition of DHT | |
|---|---|---|
| $IC_{50}$ for DHT Inhibition by: | Type 1 5α-Reductase | Inhibition type |
| 4-MA | 10 nM | Competitive |
| Finasteride | 500 nM | Competitive |
| LSESr | 2 µg/ml | Noncompetitive |

In a third paper from the same laboratory Iehlé C, Délos S, Guirou 0, Tate R, Raynaud J P, and Martin P M, in "Human Prostatic Steroid 5α-Reductase Isoforms-A Comparative Study of Selective Inhibitors" determined enzyme kinetic parameters for types 1 and 2 isoforms of 5α-reductase. Their system was an in vitro human 5α-reductase cell expression system, using Sf9 insect cells. Results are presented in Table 3.

TABLE 3

| | Enzyme Kinetic Parameters | |
|---|---|---|
| Parameter | Type 1 5α-reductase | Type 2 5α-reductase |
| Ph optima | 6–8 | 5–6 |
| Testosterone affinity, $K_m$ | 2.9 µM | 0.5 µM |
| Testosterone, $V_{max}$ | 4.2 nmoles/$10^6$ cells/min | 57.6 nmoles/$10^6$ cells/min |

TABLE 3-continued

Enzyme Kinetic Parameters

| Parameter | Type 1 5α-reductase | Type 2 5α-reductase |
|---|---|---|
| Finasteride inhibition, $K_i$ | 108 nM competitive | 7.3 nM (non)competitive** |
| LSESr inhibition, $K_i$ | 7.2 µg/ml noncompetitive | 4.9 µg/ml uncompetitive |
| Finasteride inhibition, $IC_{50}$ | 400 nN | 10.7 nM |
| LSESr inhibition, $IC_{50}$ | 4 µg/ml | 7 µg/ml |

**The authors claim this inhibition is competitive, but the data suggest it to be noncompetitive.

In this expression system, Finasteride (MK906, France) and the lipid/sterol extract of Serenoa repens, LSESr, were found to interact with human 5α-reductase in several ways (competitive, noncompetitive and uncompetitive). The LSESr interaction is suggested to result from its modulation of the 5α-reductase lipid membrane environment.

According to Niederprüm H-J et al. medium chain-length free fatty acids are responsible for the entire inhibition of 5α-reductase caused by Sabal serrulata fruit extracts. (Niederprüm H J, 1994, Phytomedicine 1:127–133). They used a supercritical $CO_2$ Sabal fruit extract as starting material, and separated this into the various lipid classes for testing in a competitive binding 5α-reductase assay using human genital skin fibroblast enzyme. Results showed that the major portion of fatty acids was present in the unesterified state. Furthermore, the nonsaponifiable material, containing the plant sterols, triterpenes and fatty alcohols, had no 5α-reductase inhibitory activity. When the extract was separated into lipid classes, the enzyme inhibition was due to neutral lipids, not glyco- or phospholipids. Linoleic, linolenic and lauric acids ($C_{18:2}$, $C_{18:3}$, $C_{12:0}$) were particularly potent inhibitors. Ethyl esters (particularly ethyl laurate) were markedly less effective than their respective free fatty acids in this system.

A nonclinical study in castrated rats compared the 5α-reductase interactions of Finasteride (Proscar) and Permixon (and other commercial plant extracts). In this study, Rhodes L, et al. found that Proscar (but not Permixon) inhibits 5α-reductase (Rhodes L, 1993, The Prostate 22:43–51). For Permixon, they found no antiandrogenic activity in rats (no inhibition of labeled DHT binding to androgen receptor). Based on these findings, they concluded it is unlikely that Permixon and other plant extracts shrink the prostate by inhibiting androgen action or 5α-reductase activity.

Steroid Mechanism of Action (Other Than 5α-Reductase)

el-Sheikh M M, Dakkak M R, and Saddique A, reported "The Effect of Permixon on Androgen Receptors" in 1988, Acta Obstet Gynecol Scand. Acta Obstet Gynecol Scand 1988;67:397–399. They studied androgen receptor binding in 11 extracts of several human tissues, in which uptake of radioactive testosterone (T) or DHT by human androgen cytosol receptors was measured in the presence or absence of Permixon. Permixon at a fixed concentration reduced the uptake of T and DHT by 41–42% in all tissues. The authors acknowledge a finding by Permixon's French manufacturer that one physiological effect in animals is reduction of capillary permeability. They concluded, however, that Permixon is antiandrogenic and suggest that a possible future use might be in management of female hirsutism, acne, polycystic ovary syndrome and other female endocrine disorders.

Sultan C, et al., in their paper entitled "Inhibition of Androgen Metabolism and Binding by a Liposterolic Extract of 'Serenoa Repens B' in Human Foreskin Fibroblasts" J steroid Biochem 1984;20(1):515–519, used an in vitro system consisting of cultured human foreskin fibroblasts to show that Serenoa repens inhibits 5α-reductase, 3-ketosteroid reductase, and binds competitively to the androgen receptor. Based on these in vitro results, they suggested that Serenoa repens may be useful as an antiandrogen for the treatment of BPH and hirsutism.

Using an in vitro system to study Permixon™ binding to the rat prostate cytosolic androgen receptor, Carilla E, et al. reported that the $IC_{50}$ for Permixon binding to the rat cytosol androgen receptor is 367 µg/ml, and that binding is competitive. Carilla E, et al. J steroid Biochem 1984;20(1):521–523. The authors commented, in response to a report that Permixon inhibits 5α-reductase, that the overall anti-prostatic activity may be multifocal, but that Permixon certainly is antiandrogenic.

In a very early pivotal paper, Elghamry M I, and Hansel R used mouse uterus to study the activity of an isolated phytoestrogen of saw palmetto fruits (Serenoa repens Small), which at that time was a new estrogenic plant. Elghamry M I, Experientia 1969; 25(8):828–829. The authors showed that crude and partially purified extracts of Serenoa repens berries were estrogenic (caused uterine hypertrophy) following injection into immature mice. They showed that this estrogenic effect was similar to that of β-sitosterol, but that much higher doses of the Serenoa extract (1000-fold) were needed. They tried but failed to show a dose-response relationship for the Serenoa extract.

Anti-inflammatory Mechanism of Action

Breu W, et al. studied the anti-inflammatory activity of Sabal fruit extracts prepared with supercritical carbon dioxide (SG 291, e.g. Talso, Talso uno). Breu W et al. Arzneim-Forsch/Drug Res 1992;42:547–551. Specifically, the authors studied the inhibitory effects of SG 291 on the biosynthesis of inflammatory and edematous arachidonic acid metabolites produced by the cyclooxygenase (CO) and 5-lipoxygenase (5-LO) pathways. The $IC_{50}$ of SG 291 was found to be 28.1 µg/ml for CO, and 18 µg/ml for 5-LO. They fractionated SG 291 into acidic lipophilic Fractions A, B and C, and determined that Fraction A (the fatty alcohol fraction) accounted for all of the anti-inflammatory and antiedematous activity of SG 291. Their conclusion is that SG 291, which is prepared from Sabal serrulata (syn. Serenoa repens), has demonstrated anti-inflammatory and anti-edematous properties which may aid in alleviating symptoms of BPH.

Antiedematous properties of a hexane extract of the fruit of Serenoa repens Bartr. were examined in pharmacological studies in rats and guinea pigs carried out by Tarayre J P, et al. Ann Pharm Fr 1983;41(6): 559–570. The researchers used a research laboratory-prepared hexane extract of Serenoa repens Bartr to show a decrease in histamine 48/80- and dextran-induced capillary permeability, dextran-generalized edema, IgE-dependent passive cutaneous anaphylaxis in rats, centrifugation-induced tail edema in mice and UV-induced erythema in guinea pigs. Adrenal involvement was ruled out as a mechanism for these observations, as were serotonin and bradykinin pathways. In their hands, this laboratory-prepared extract of Serenoa repens Bartr displayed unequivocal antiedematous properties in several rodent models.

Wagner H and Flachsbarth H purified and biochemically characterized a saw palmetto berry fraction which showed rat paw edema inhibition (anti-inflammatory and antiedematous). Wagner H and Flachsbarth H *Planta Med* 1981;41:244–251. In their paper, they described the purification of an acidic polysaccharide from an aqueous extract of *Sabal serrulata* Roem. et Schult. (*Serenoa repens* Bart.). Molecular weight is 100,000 daltons with main sugar components being galactose (38%), arabinose (18.7%) and uronic acid (14%).

Immunostimulating Mechanism of Action

Wagner H, et al., made in vitro comparisons of various immune function indicators using extracts of higher plants. The investigators purified water or alkaline-water extracts of many plants (including *Sabal serrulata* Roem et Schult.) and tested them in granulocyte and carbon clearance tests. Molar ratios of the polysaccharide heteroglycan constituents of the various plant extracts relative to arabinose are listed in the paper. For *Sabal serrulata*, these values are: rhamnose (0.1), xylose (0.9), arabinose (1), mannose (0.1), galactose (1.5), and glucose (0.6). In the granulocyte clearance test, a relatively high concentration of the *Sabal serrulata* was required.

Muscle Relaxant Mechanism of Action

Gutierrez M et al. described a muscle relaxant mechanism for the symptomatic relief of urinary dysfunction by extracts of *Sabal serrulata* fruit. Using rat uterus, urinary bladder, and aorta, they showed a reversal of agonist-induced in vitro smooth muscle contraction following exposure to *Sabal serrulata* extracts (Gutierrez M., *Gen Pharmac* 1996;27(1) :171–176). The significance of these findings is that the most relevant clinical effect of Sabal in the treatment of BPH is the alleviation of symptoms (increased urinary flow, decreased dysuria, and decreased hypogastric discomfort), resulting in an increased feeling of well-being. Because these beneficial effects occur in the absence of a modification in prostate size, the authors feel that they may be due to smooth muscle relaxant actions following treatment with Sabal. Their evidence is presented below.

The effects of two extracts from *Sabal serrulata* fruits (total lipidic [L] and saponifiable [S]) on smooth muscle contractions were examined. At 0.1–1 mg/ml, both extracts relaxed the tonic contraction induced by norepinephrine (30 nM) on rat aorta ($EC_{50}$=0.53±0.05 mg/ml [L] and 0.5±0.04 mg/ml [S]); and by KCl (60 $\mu$M) on rat uterus. The Sabal extracts (0.3–1 mg/ml) also antagonized the dose-response curve of rat urinary bladder contractions induced by acetylcholine (0.1–100 $\mu$M).

L-propranolol (1 $\mu$M), but not the inactive R-propranolol (1 $\mu$M), potentiated the Sabal extracts' relaxant effects by lowering the $EC_{50}$ (0.35±0.2 vs 0.20±0.01 mg/ml for [L] and 0.43±0.02 vs 0.19±0.02 mg/ml, p<0.01, for [S] extract). Cycloheximide (10 $\mu$g/ml) antagonized the effects of extracts from Sabal. However, actinomycin D (5 $\mu$g/ml) significantly (p$\leq$ to 0.01) antagonized the effect of the total lipidic extract without modifying that of the saponifiable extract. The relaxant effect of both extracts was not modified by the tyrosine kinase inhibitor genistein (10 $\mu$M) or the ornithine decarboxylase inhibitor a-difluoromethylornithine (10 mM).

The underlying mechanism of action is thought to result from inhibition of the influx of calcium ions into smooth muscle cells. The investigators showed that the relaxant effect depends on the induction of transcription and protein synthesis, and their evidence argues against a mechanism involving $\beta$-adrenergic receptor activation, polyamine involvement or tyrosine phosphorylation.

From these data, they conclude that smooth muscle relaxation of prostate tissue following treatment with extracts from *Sabal serrulata* berries improves in patient's urinary symptoms and feeling of well-being. It is noteworthy that a number of pharmaceuticals labeled for mitigation of the urinary dysfunction associated with BPH rely on their smooth muscle relaxant properties for efficacy (e.g., tamsulosin [Flomax™], terazosin [Hytrin™], and doxazosin [Cardura™]).

A number of clinical studies with SPB-extracts have been published in recent years. In 1984, Champault et al. reported a double blind, placebo controlled study in 110 outpatients (Champault et al., 1984, *Br. J. Clin. Pharm.* 18:461–462). In this study, 55 patients received the SPB-extract Permixon™ (160 mg, twice daily) and 55 patients received placebo treatment for 30 days. The study reports statistically significant improvements in nocturia, intensity of dysuria, urine flow rate, and post-nicturition residue. This report records minor side effects (e.g., headaches) in 5 patients. Di Silverio et al. have reported on the treatment of 34 BPH patients with the SPB-extract Strogen Forte™ (160 mg, twice daily) for three months (Di Silverio et al., supra). The results of the study showed subjective improvements in 60% of patients and included a reduction of urine volume in 50%, a slight reduction in prostate volume in 53%, and significant increase in serum testosterone levels and reduction in intraprostatic DHT concentrations. The authors have also reviewed studies during 1983–1985 which report efficacy and tolerability of the SPB-extract Strogen Forte in BPH patients. In 1993, Romics et al. reported on a one year treatment study in 42 patients (Romics et al., 1993, *Internat. Urol. and Nephrol.* 25(6):565–569). This study reported significant improvements in objective symptoms like night urination (68.4%) residual volume (74.7%) and interrupted urine stream and post-urination dribbling in 80% of patients. No side effects were reported. In another study, Vahlensieck et al. reported a 12-week treatment study of 1334 BPH outpatients with the SPB-extract of *Sabal serrulata* (Vohlensieck et al., 1993, *Fortsch der Med.* 111(18) :323–326). Under this treatment, the volume of residual urine decreased by 50%, pollakisuria decreased on the average by 37%, and nocturia by 54%. The number of patients with dysuria pain decreased from 75% to 37%. Furthermore, they found the efficacy of the drug "good to excellent" in more than 80% of the cases and tolerability "good to excellent" in more than 95% of the patients.

Thus, Saw Palmetto is useful to treat and/or ameliorate BPH and/or urinary dysfunction. Other researchers have reported combination treatments. Specifically, SPB-extract used in combination with extracts from pumpkin seeds (53 patients) (Carbin et al., 1990, *Br. J. Urol.* 66:639–641) or urica extract (2,080 patients) (Schneider et al. 1996, *Fortsch der Med.* 113(3):37–40). All of these studies support the efficacy of SPB-extract in the treatment of BPH and/or urinary dysfunction.

3. SUMMARY OF THE INVENTION

This invention provides a method for making a pharmaceutical grade of botanical drug, for example saw palmetto. The method is the process of PharmaPrinting™. In one embodiment, the method comprises the steps of: providing a botanical material of saw palmetto which comprises a plurality of components which have a given biological activity; removing a representative aliquot from the botanical material; separating the aliquot into a plurality of marker fractions wherein each of the marker fractions comprises at least one of the active components; determining the degree of the given biological activity for each of the marker fractions to provide a bioactivity fingerprint of the aliquot; and comparing the bioactivity fingerprint of the aliquot to a bioactivity fingerprint standard which has been established for a pharmaceutical grade saw palmetto to provide a bioactivity fingerprint comparison to determine whether the botanical material is a pharmaceutical grade saw palmetto based on the bioactivity fingerprint comparison.

This invention also provides a method comprising the steps of: providing a botanical material of saw palmetto which has a given biological activity, said botanical material comprising a plurality of components; separating a representative aliquot of the botanical material into a plurality of marker fractions wherein at least one of the marker fractions comprises at least one active component; determining the degree of the given biological activity for each of the marker fractions to provide a bioactivity fingerprint of the representative aliquot; and comparing the bioactivity fingerprint of the representative aliquot to a bioactivity fingerprint standard which has been established for a pharmaceutical grade saw palmetto to determine whether the botanical material is a pharmaceutical grade saw palmetto.

In one embodiment, one or more of the marker fractions contain one active component.

The method may also comprise the additional steps of: determining the amount of the active components in each of the marker fractions to provide a quantitative compositional fingerprint of the aliquot and comparing both the quantitative compositional and bioactivity fingerprints with a quantitative compositional and bioactivity fingerprint standard to determine whether the botanical material is a pharmaceutical grade saw palmetto. The method may also comprise the additional steps of: determining a total bioactivity of the aliquot of the botanical material and comparing the total bioactivity of the aliquot with that of a total bioactivity of a standard which has been established for a pharmaceutical grade saw palmetto.

The invention also provides a method for making a pharmaceutical grade saw palmetto, the method comprising the steps of: providing a botanical material of saw palmetto which comprises a plurality of components which have a given biological activity and wherein each active component has a standardized bioactivity profile; removing a representative aliquot from the botanical material; separating the aliquot into a plurality of marker fractions wherein each of the marker fractions comprises at least one of the active components; measuring the amount of each of the active component(s) present in each of the marker fractions; calculating the bioactivity of each of the marker fractions based on the amount of each active component present and the standardized component bioactivity profile to provide a calculated bioactivity fingerprint of the aliquot; comparing the calculated bioactivity fingerprint of the aliquot to a bioactivity fingerprint standard which has been established for a pharmaceutical grade saw palmetto to provide a bioactivity fingerprint comparison to determine whether the botanical material is a pharmaceutical grade saw palmetto is obtained based on the bioactivity fingerprint comparison.

The method of the invention is useful to make a pharmaceutical grade botanical material, e.g., saw palmetto from an appropriate botanical material which has a given or desired biological activity. Preferably, the botanical material is an extract made from plant material such as an aqueous or organic extract such as an alcoholic extract or a supercritical carbon dioxide extract or organic solvent extract which may be subject to further processing. Alternatively, the botanical material is a powdered plant material, a seed oil, an essential oil or the product of steam distillation. In one embodiment, the botanical material is a homogeneous material in a single physical state, e.g. an oil or a solution. The botanical material may be a pure material derived solely from the botanical of interest.

In an alternative embodiment, saw palmetto may be combined with one or more botanical materials selected from: aloe, Asian ginseng, astragalus, bilberry, black cohosh, burdock, chamomile, chestnut, coriolus versicolor, couchgrass, crampbark, dandelion root, dong quai, echinacea, elecampane, evening primrose, eyebright, false unicorn root, feverfew, garlic, ginger, ginkgo, goldenseal, gota kola, grape seed extract, green tea, guggulipid, hawthorn, hops, ivy, kava, licorice, milk thistle, mistletoes (American, Asian and European varieties), motherwort, oats, osha, passion flower, pumpkin, pygeum, red clover, rosemary, Siberian ginseng, sarsaparilla, saw palmetto, skullcap, St. John's wort, stinging nettle, valerian, wild indigo, wild yam, and yerba mansa. The methods of the present invention for making pharmaceutical drugs encompass methods for PharmaPrinting™ saw palmetto plus one or more of the botanicals listed above as well as pharmaceutical grade drugs containing saw palmetto and one or more of the botanicals listed above. In one embodiment, saw palmetto may be combined with couch grass, stinging nettle root, pumpkin seeds, and/or pygeium.

By way of illustrative example, but not by way of limitation, pharmaceutical grade saw palmetto may be combined with a pharmaceutical grade botanical material such as black cohosh or St. John's wort. See, for example, U.S. patent application, Ser. No. 08/838,198, entitled "PHARMACEUTICAL GRADE PHARMACEUTICAL DRUGS," filed Apr. 15, 1997; for pumpkin, see, Example 32, pages 182–183; for pygeum, see Example 33, pages 183–185; for stinging nettle, see Example 36, pages 188–190; incorporated in its entirety by reference herein.

In this invention the active component(s) include, but are not limited to, one or more of the following chemical classes: acetogenins, alkaloids, carbohydrates, carotenoids, cinnamic acid derivatives, fatty acids, fatty acid esters, flavonoids, glycosides, isoprenoids, lipids, macrocyclic antibiotics, nucleic acids, penicillins, peptides, phenolics, polyacetylenes, polyketides, polyphenols, polysaccharides, proteins, prostaglandins, steroids and terpenoids.

The bioactivity/clinical indication for the saw palmetto may be associated with a disease, disorder or condition of humans or other animals. Thus the methods are useful to produce pharmaceutical grade saw palmetto for treatment and/or amelioration and/or prevention of human and/or veterinary diseases, disorders or conditions. Exemplary indications include, but are not limited to, alleviation of symptoms of benign prostatic hypertrophy.

In these methods, the aliquot may be separated into both biologically active and inactive components. Furthermore, the marker fractions may comprise a class of related components.

This invention also provides a method of preparing a PharmaPrint® for a pharmaceutical grade botanical, e.g., saw palmetto. Furthermore, this invention provides for a pharmaceutical grade botanical, e.g., saw palmetto prepared by the methods described herein.

3.1. Definitions

The term "pharmaceutical grade" when used in this specification means that certain specified biologically active and/or inactive components in a botanical drug must be within certain specified absolute and/or relative concentration range and/or that the components must exhibit certain activity levels as measured by a disease-, disorder- or condition-specific bioactivity assay. The disease, disorder or condition may afflict a human or an animal.

As will be understood by those skilled in the art, the term "pharmaceutical grade" is not meant to imply that the botanical drug is applicable only to products which are regulated for example those provided under prescription, i.e., "Rx" products or over the counter, i.e., "OTC". The term is equally applicable to products provided as Rx, OTC or as a dietary supplement, i.e., "DSHEA".

As used herein "components" means discrete compounds (i.e. chemicals) which either are present naturally in a botanical drug or have been added to the botanical drug so as to prepare a pharmaceutical grade botanical drug having components within a defined bioactivity range(s) and/or compositional range(s).

As used herein "active components(s)" means one or more component(s) for which the summation of the individual component(s) activity in a disease-specific bioassay accounts for a substantial portion of the observed biological activity of the botanical material. Preferably, the summation of the active components' activities accounts for the majority or greater than 50% of the observed biological activity.

As used herein "fractions" typically means a group of components or class of structurally similar components having defined parameters such as solubility, molecular weight range, polarity range, adsorption coefficients, binding characteristics, chemical reactivity or selective solubility. Most frequently fractions will be the product of selective solvent solubility and partition techniques (i.e. liquid-liquid extraction) including pH dependent separations, chromatographic separation techniques, i.e., flash chromatography, preparative high performance liquid chromatography (HPLC), preparative gas chromatography, partition chromatography, preparative thin layer chromatography, affinity chromatography, size exclusion chromatography, liquid-liquid chromatography e.g., counter-current chromatography or centripetal or centrifugal chromatography.

The present invention may be understood more fully by reference to the detailed description of the invention and examples of specific embodiments and the appended figures.

4. BRIEF DESCRIPTION OF THE DRAWINGS

Figure 4:
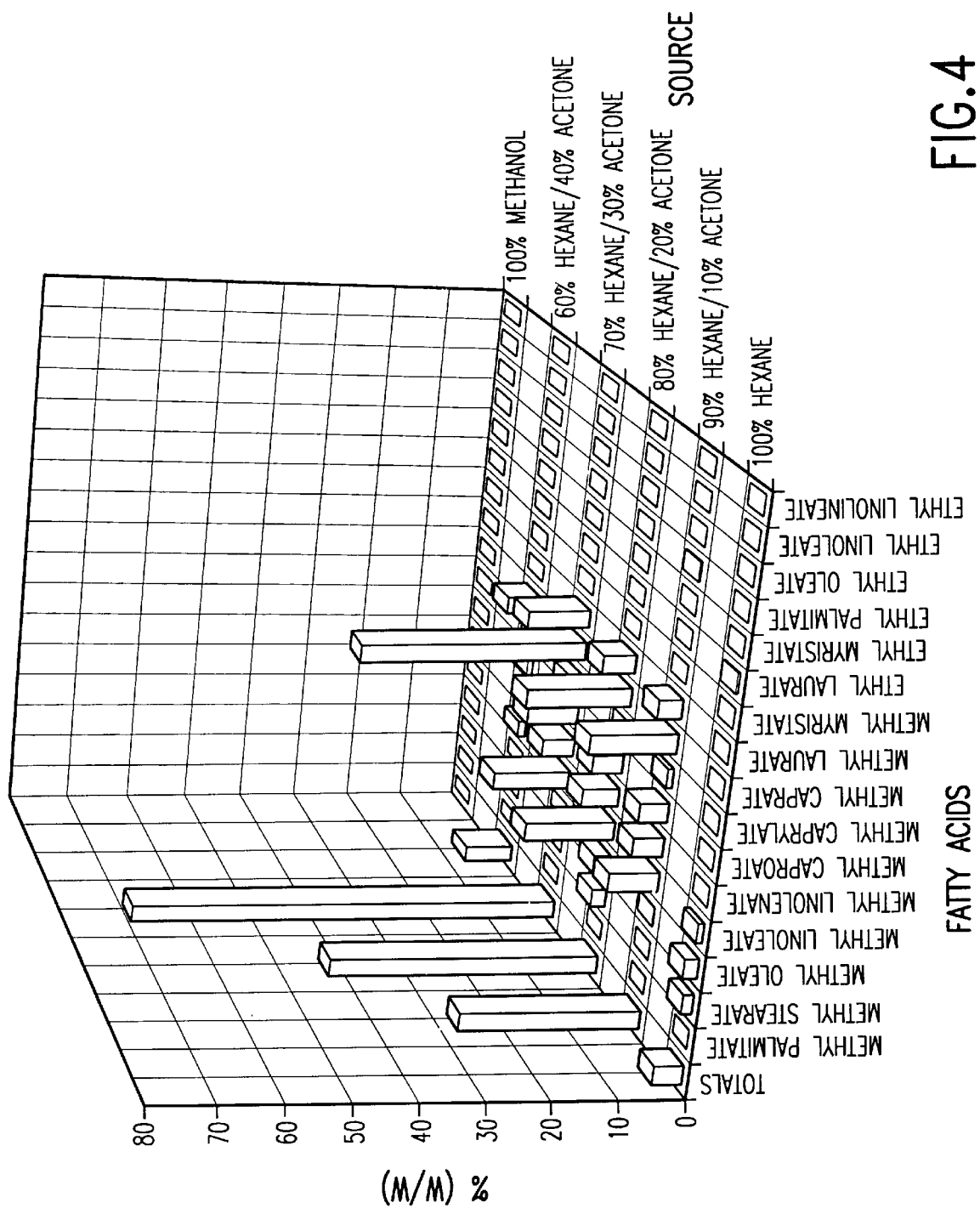

FIG. 4 shows the result of the fractional analysis for Saw Palmetto from a commercially available product. The vertical axis is in weight/weight percent. The two axes are the fractions of the various fatty acids and fatty acid esters and the solvent system.

Figure 5:
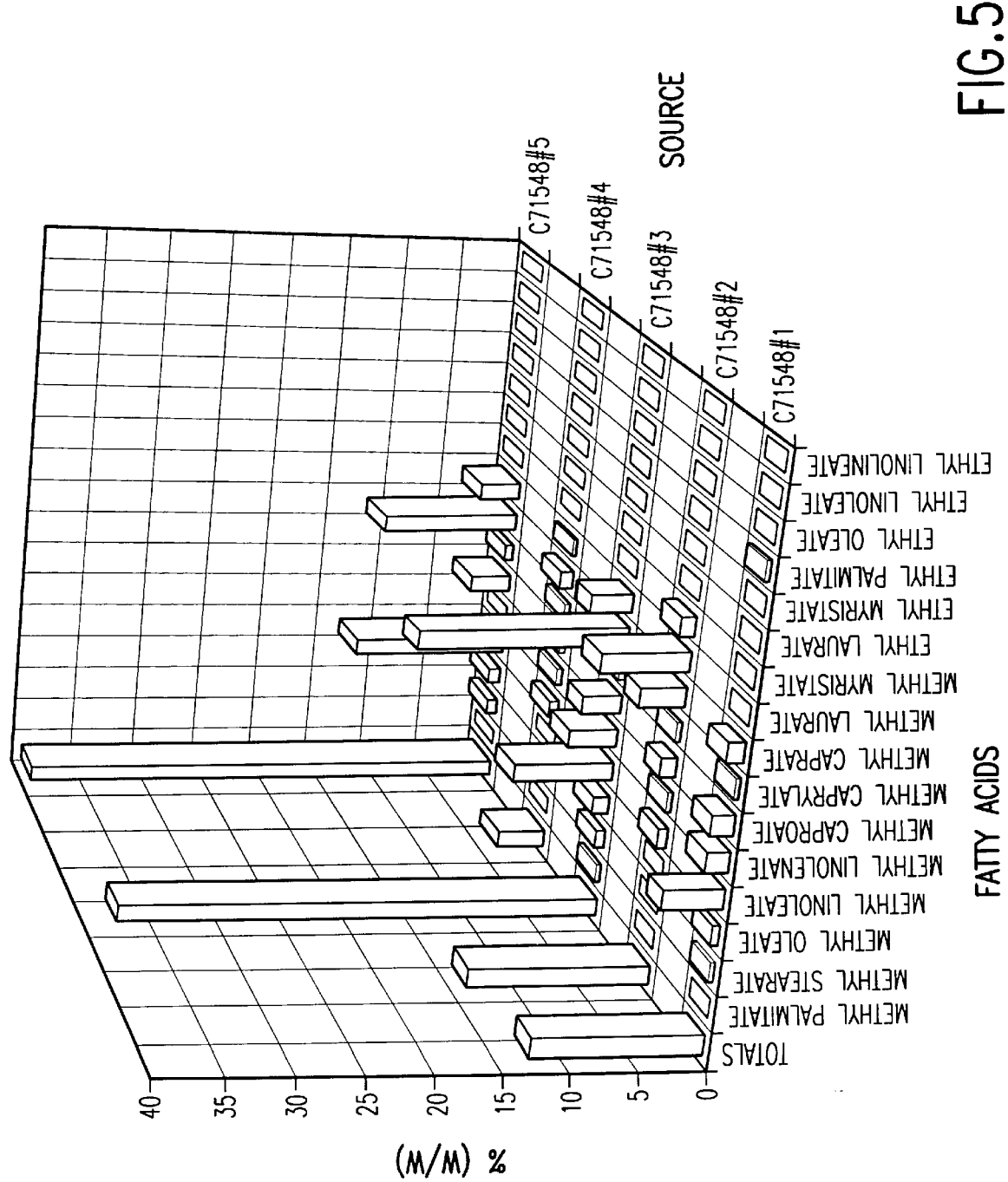

FIG. 5 shows the chemical analysis of five different commercially available Saw Palmetto products. The vertical axis is in weight/weight percent. The other axes are the fatty acids and fatty acid esters and the source material.

Figure 6:
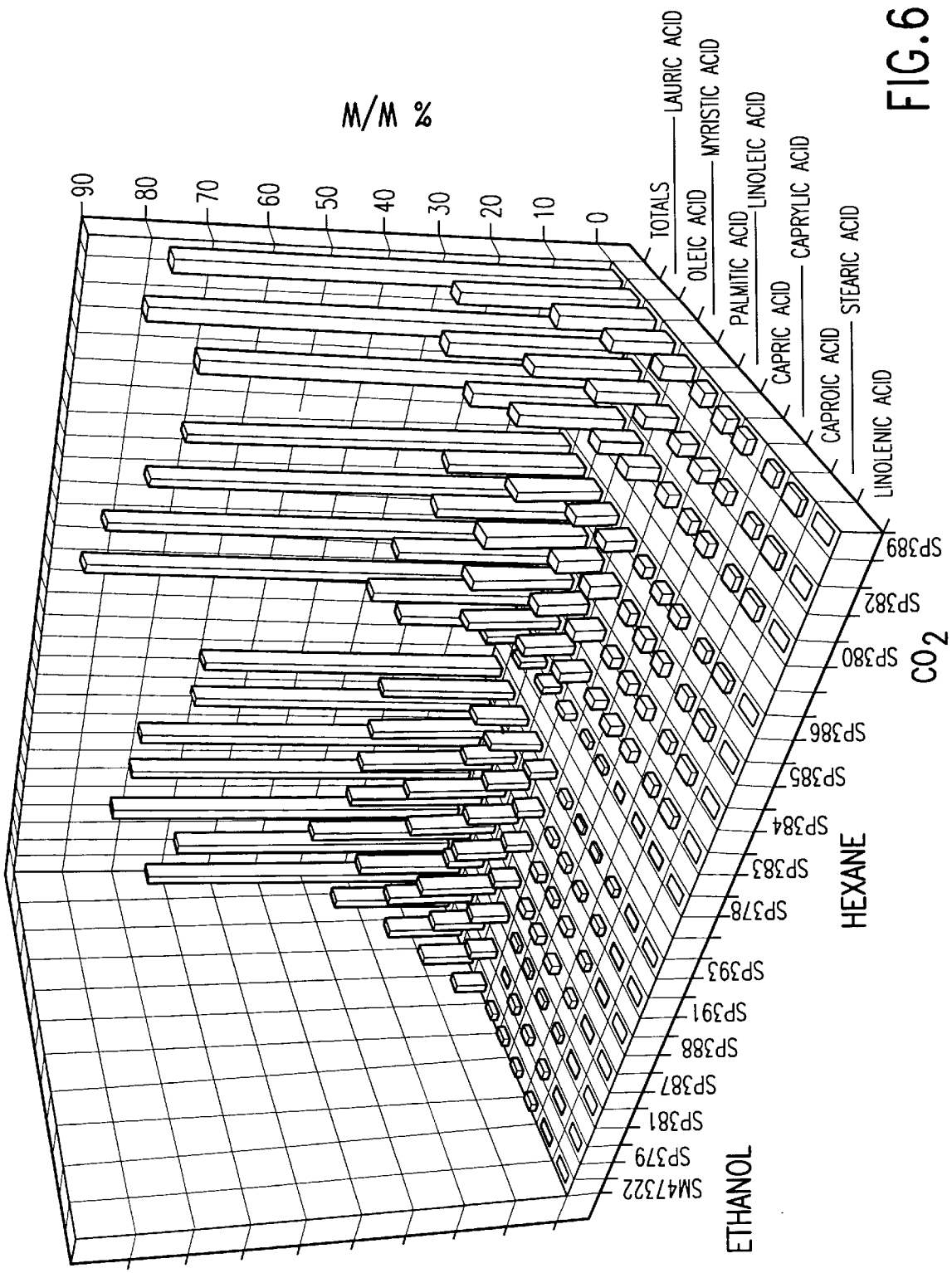

FIG. 6 shows the fatty acid analysis of saw palmetto extracts prepared by ethanol, hexane or supercritical $CO_2$ extraction. The vertical axis is in weight/weight percent. The other axes are the fatty acids and fatty acid esters and the source material.

Figure 7:
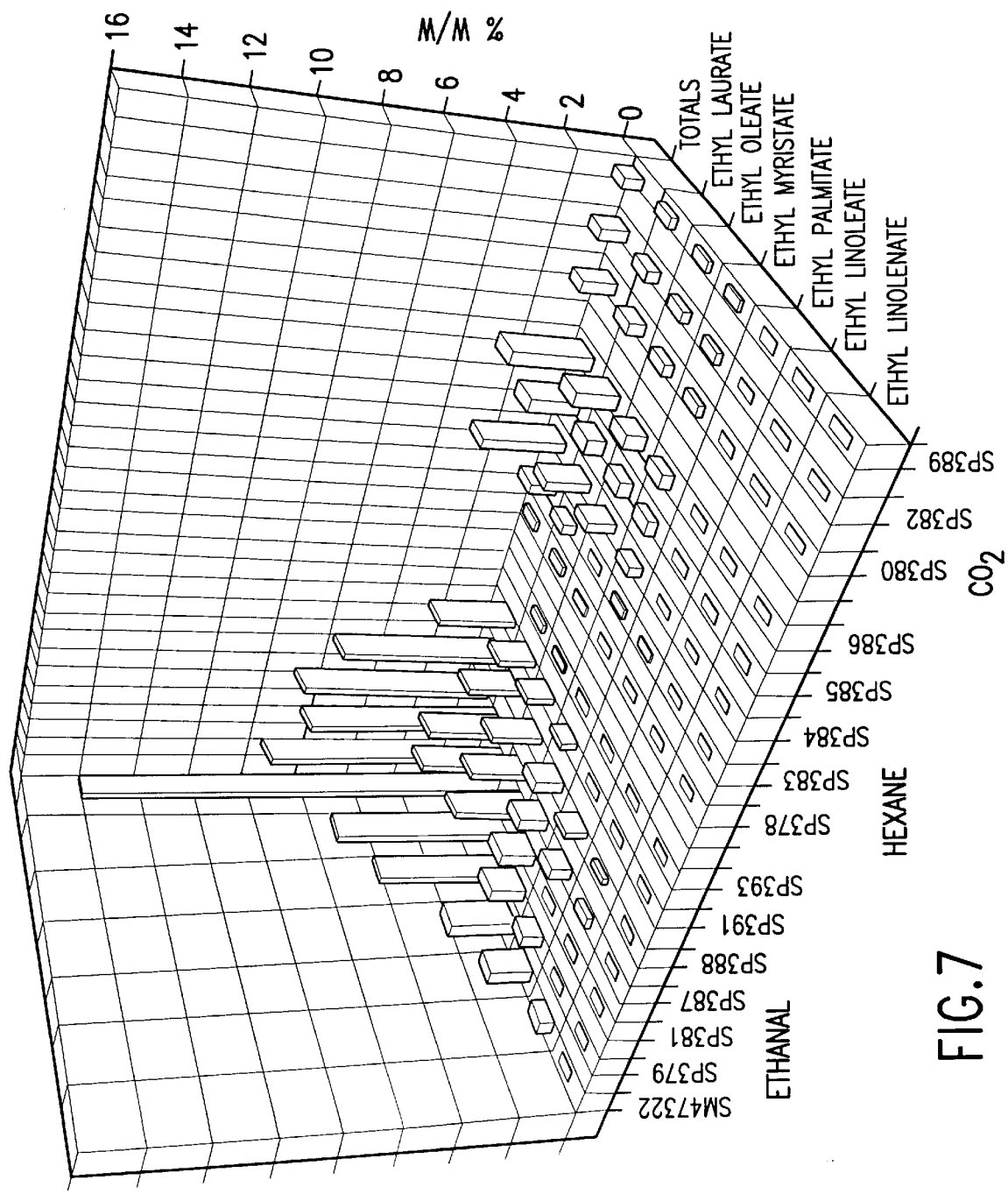

FIG. 7 shows the ethyl ester analysis of saw palmetto extracts prepared by ethanol, hexane or $CO_2$ extraction. The vertical axis is in weight/weight percent. The other axes are the fatty acids and fatty acid esters and the source material.

Figure 8:
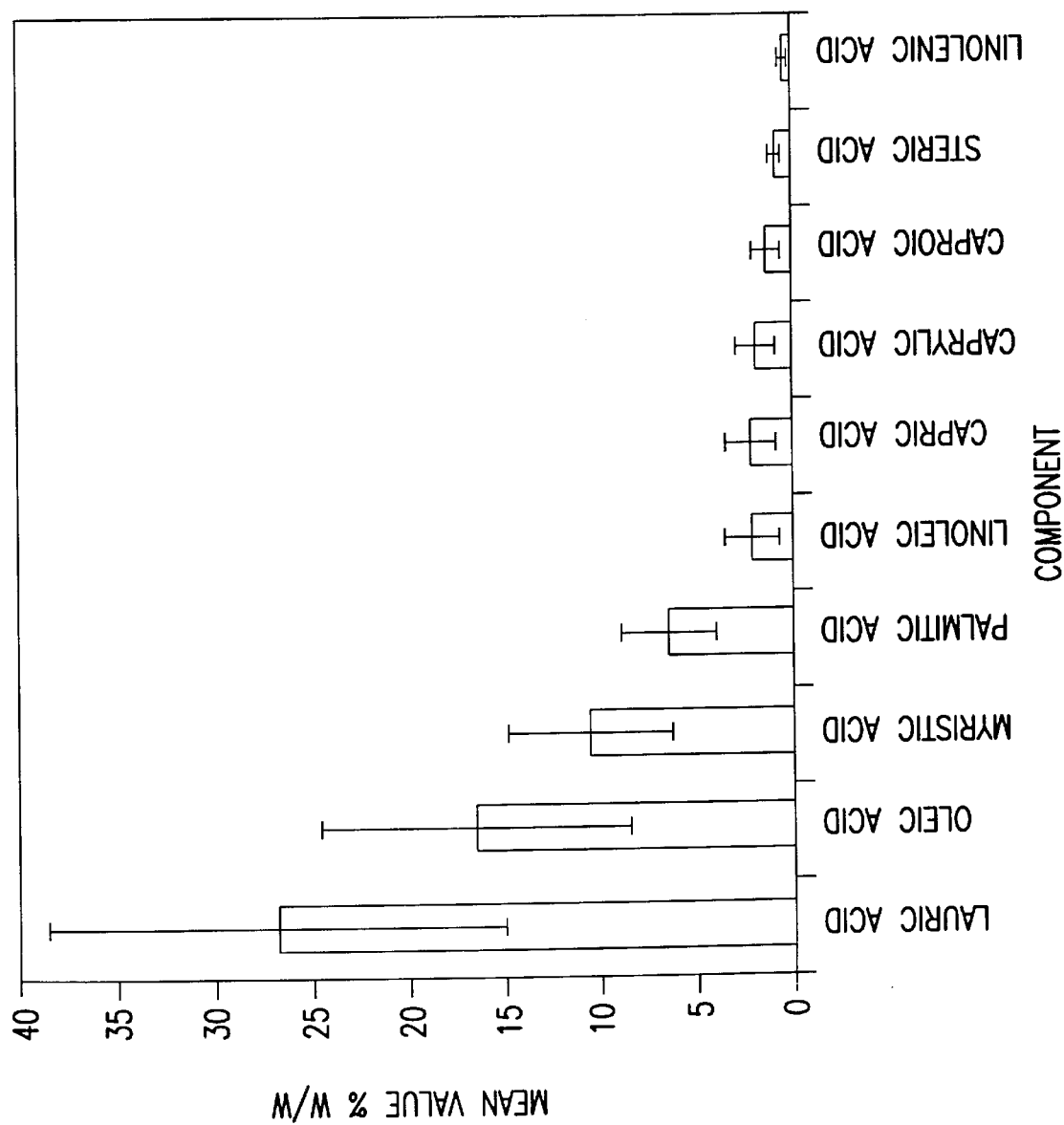

FIG. 8 shows the mean value ±SD (in weight/weight %) of the components of various saw palmetto samples.

5. DETAILED DESCRIPTION OF THE INVENTION

5.1. Methods of Pharmaprinting™

The present invention provides a method for producing botanical drugs which may be classified as being of pharmaceutical grade. The method is designated PharmaPrinting™. The pharmaceutical grade botanical drugs made by the method of the present invention are particularly well-suited for use in clinical studies and more importantly for use in treatment of patients. The method insures that the drug being used for a particular protocol will be of consistent quality and consistently suitable for use as human and veterinary prophylactic or therapeutic agents.

The present invention provides the ability to closely control the quality, dosage and clinical effectiveness of botanical extracts and other botanical materials, e.g., botanical extract and mammalian tissue derived biological preparation. One aspect of the present invention involves the establishment of the chemical and/or bioactivity fingerprint standards for various botanical materials. Once established, the fingerprint standards are used in drug production procedures to insure that the botanical materials meet pharmaceutical grade requirements. Specific quantitative and biological fingerprints are presented which have been established for a number of botanical materials as a further aspect of the invention. These fingerprints are useful for determining if a particular botanical material meets levels of pharmacological activity and composition requirements for a particular treatment regimen. Such a determination is important to insure that clinical studies and patient treatment with the botanical materials are based on consistent and verifiable extract composition parameters.

This invention is useful in providing botanical materials which are sufficiently characterized and whose compositions are consistent between batches, so that they can be precisely dosed and used effectively in clinical settings. The methods described herein provide an assurance that the results of a clinical trial will be reproducible.

Initially, a sample of the botanical material of interest, for example, saw palmetto, is obtained. Many botanicals are commercially available as the raw material or as a processed extract. Often it is a botanical extract or other composition which is intended for use as a drug. The processed material may include a plurality of active components which exhibit a given biological activity and plurality of inactive components which do not directly exhibit the biological activity of interest. In one embodiment, an aliquot is removed from the botanical material and subjected to a quality assurance or standardization procedure. Preferably, the aliquot is a representative aliquot of a homogeneous botanical material. The procedure involves separating the aliquot of botanical material into a plurality of marker fractions wherein each of the marker fractions includes at least one of the active components or in some cases one of the inactive components. The amount of active component or inactive component in each of the marker fractions is determined in order to provide a quantitative fingerprint of the aliquot. The degree of biological activity for each of the marker fractions is also determined to provide a biological activity fingerprint for the aliquot.

The chemical and/or biological activity fingerprints of the aliquot are then compared to corresponding fingerprints which have been established for a pharmaceutical grade drug. If the fingerprints of the botanical match the standard fingerprints, then the botanical is identified as a pharmaceutical grade botanical drug. If not, then the botanical may be modified so as to provide a match with the standard fingerprints or may be rejected.

5.1.1. METHODS OF DEVELOPING A PHARMAPRINT®

The method of developing a PharmaPrint® for a botanical when a range of putative active components is known begins with a literature review. It involves reviewing the chemical literature, the biological literature, the published bioassays and clinical data for the botanical. Particularly useful sources of information are the NAPRALERT computer database managed by Dr. Norman Farnsworth in the Program for Collaborative Research in the Pharmaceutical Sciences, University of Illinois, Chicago; Leung and Foster, *Encyclopedia of Common Natural Ingredients Used in Food, Drugs and Cosmetics*, 2nd Ed. John Wiley & Sons: New York, N.Y., 1996; *Herbal Drugs and Phytopharmaceuticals*, ed. N. G. Bisset, CRC Press: Boca Raton, Fla., 1994; Duke, *Handbook of Biologically Active Phytochemicals and Their Activities*, CRC Press: Boca Raton, Fla., 1992; Tyler and Foster "Herbs and Phytomedicinal Products" in *Handbook of Nonprescription Drugs* Berardi et al. eds., United Book Press, Inc.: Washington, D.C., 1996. For a given indication, the literature must be studied to confirm that the putative active components are actually associated with that disease state. In addition, if there are any bioassays known for the putative active components and known for the indication, the bioassays must be consistent with both the indication and the putative active components. The appropriate bioassay(s) is tied to a clinically relevant endpoint(s). The bioassay(s) should be quantitative over a wide concentration range. Typically, an $IC_{50}$ curve (Inhibitory Concentration 50%), $EC_{50}$ (Effective Concentration 50%), or an appropriate $K_i$ or $K_d$ (dissociation constant of the enzyme and its inhibitor) curve is prepared. A thorough chemical and biological analysis of both putative active components and chromatographic fractions of the botanical is then performed. The results are analyzed to prepare a quantitative analysis of the biological activity for each of the chemical components in the sample. Then, the bioactivity of the sample as a whole is compared to the bioactivity of the individual components. At this point the individual chemical components can be correlated with a clinically relevant endpoint. Similar methodologies may be applied to bioassays measuring stimulatory or inhibitory effects.

Based on activity of the components individually and knowing the total activity, the components should, when combined, account for a substantial portion of the biological activity. Generally, the combined activity will account for at least 25% of the total activity.

Preferably, the summation of the individual active components' activities account for the majority or greater than 50% of the observed biological activity. More preferably, the isolated individual components are responsible for more than 70% of the activity. More preferable still, the isolated individual components are responsible for greater than 80% of the biological activity.

Another consideration will be to select as few active components as possible to be part of the PharmaPrint™. Fewer active components are important for practical considerations in raw material acceptance and manufacturing. In this invention, a correlation is established between the relevant chemical components and the bioactivity. Once a satisfactory correlation is established, it may not be necessary to perform the biological fingerprints on each sample. Rather, a chemical analysis of the appropriate components and/or marker fractions of each sample of the botanical of interest will suffice to account for most of the biological activity and establish that a given botanical sample is pharmaceutical grade.

In one embodiment, the present invention may involve one of the following procedures. One procedure, as schematically outlined in FIG. 1, involves establishing the compositional and bioactivity fingerprint standards for a given pharmaceutical grade botanical drug. Once the fingerprint standards are established, then the actual processing of the botanical into a pharmaceutical grade drug can be carried out as schematically outlined in FIG. 2.

Figure 1:
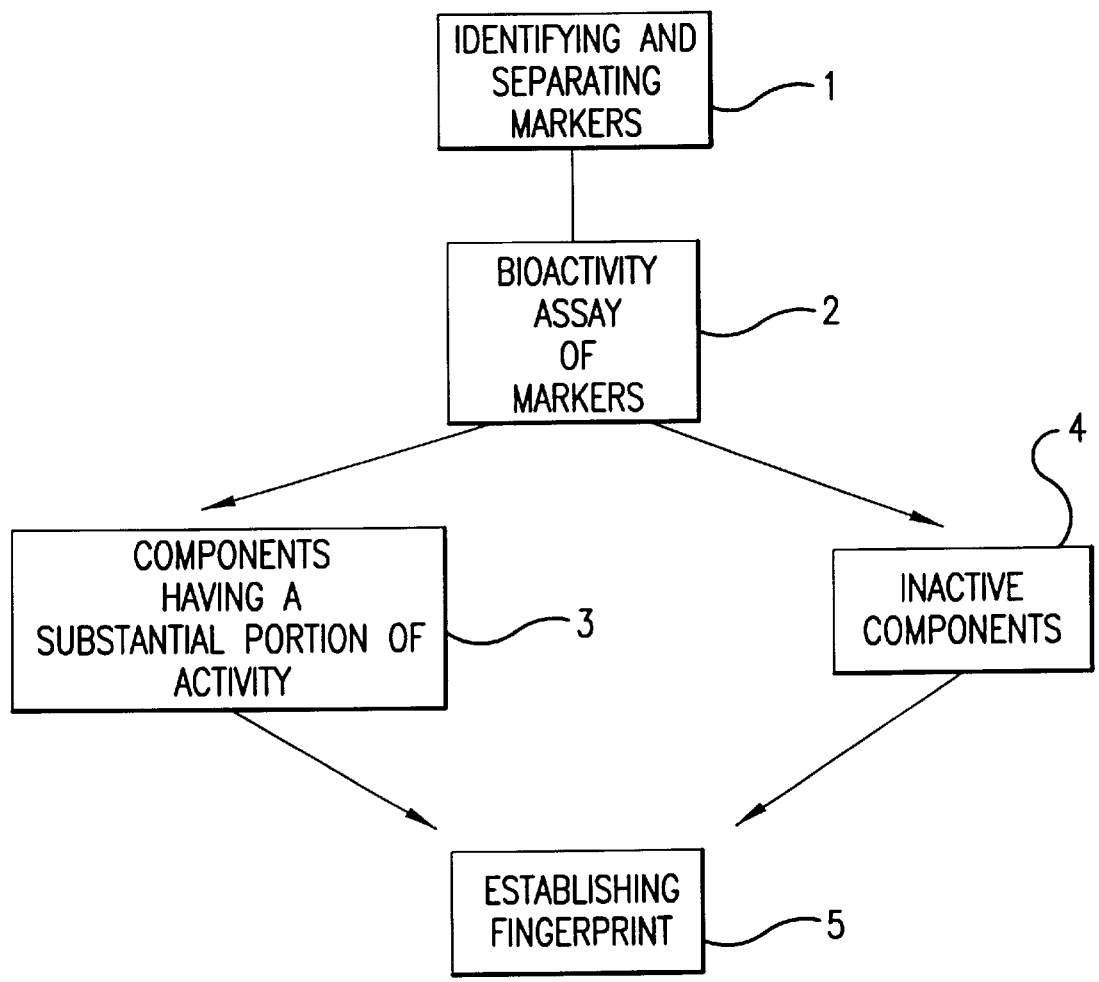
FIG. 1 is a schematic representation of a procedure in accordance with the present invention which is used to establish standard chemical and/or bioactivity fingerprints against which subsequent processed botanical materials are compared during production of pharmaceutical grade drugs.

The initial step in establishing the chemical and/or bioactivity fingerprint for a given botanical involves separating the extract or powder into one or more groups as represented by step 1 in FIG. 1. These groups are separated out and identified based on their potential as markers (which may or may not comprise active components) for the fingerprint which is to be established for the processed botanical material. The putative components or groups of putative components which are chosen and identified as potential markers will vary widely depending upon the botanical being processed and the pharmaceutical use. There should be at least two putative markers selected for each botanical. The number of potential markers may be more than five and can be as high 15 to 20 or more for complex botanical extracts or powders. The potential markers are identified and selected, for the most part, based on their potential biological activity or contribution to biological activity for a given pharmaceutical application. For a different indication the same botanical may be used for preparing an extract with a different extraction procedure in order to optimize specific bioactive constituents. Markers which have no apparent biological activity by themselves may be separated out and may be included as markers for use in the fingerprint. These "proxy" markers may be desirable as an internal standard where the markers' presence is indicative of other active components necessary to provide a substantial portion of the overall observed biological activity for the botanical drug. They also help to assure proper botanical identity of the drug (i.e. chemotoxonomy).

The initial separation of the botanical into various groups of putative markers is accomplished by conventional separation techniques ranging from simple extraction and partition, to complex affinity chromatographic techniques, including gel filtration chromatography, flash silica gel chromatography and reverse phase chromatography. Once the putative markers have been identified for a given botanical, then the bioactivity of each of the markers is determined as depicted by step 2 in FIG. 1. The particular bioassay used to determine bioactivity of the botanical is chosen based upon the intended use for the botanical. The bioassay preferably will provide a reflection of the putative markers' bioactivity with respect to the condition or indication which is to be treated with the botanical.

The bioassay results obtained in step 2 are used to identify the components having the desired bioactivity (step 3) and those which are less active or essentially inactive (step 4). Each of the groups identified in steps 3 and 4 is then analyzed quantitatively to determine the amount of each identified component present in each group. The results of the bioassays and quantitative compositional assays are then used to prepare a bioassay fingerprint and/or a chemical fingerprint for the botanical as depicted by step 5 in FIG. 1. As part of establishing the fingerprints for the botanical, acceptable ranges of bioactivity and/or chemical composition are determined. This is done primarily based upon establishing acceptable ranges of bioactivity and quantitative amounts for each marker which provide for the desired pharmacological activity of the processed material as a whole.

In addition, various combinations of active and inactive marker fractions may be evaluated to establish potential increases in desired bioactivity resulting from combinations of the active and inactive components.

The bioassay and quantitative fingerprints which are established in step 5 provide an accurate identification of the botanical which can be used in establishing the dosage regimens and treatment schedules which are necessary for clinical use. The dosage regimens and treatment schedules are established using conventional clinical methods which are commonly employed when investigating any new drug. The processed material which is used to determine the dosage and treatment schedules must be matched with and meet the requirements of the fingerprints established in step 5. This method insures that the dosage and treatment schedules are effective and reproducible since the processed materials used in the dosage and scheduling studies all have the same fingerprints in accordance with the present invention.

The bioassay and quantitative fingerprints which are determined by the general procedure as set forth in FIG. 1 are used as part of the manufacturing procedure for producing pharmaceutical grade botanical drugs. The fingerprints are used as part of a quality assurance or standardization procedure to insure that a given botanical contains the appropriate compounds and is processed correctly to provide a botanical drug which will perform the same clinically as the material which has been standardized and tested in accordance with the procedure set forth in FIG. 1.

Figure 2:
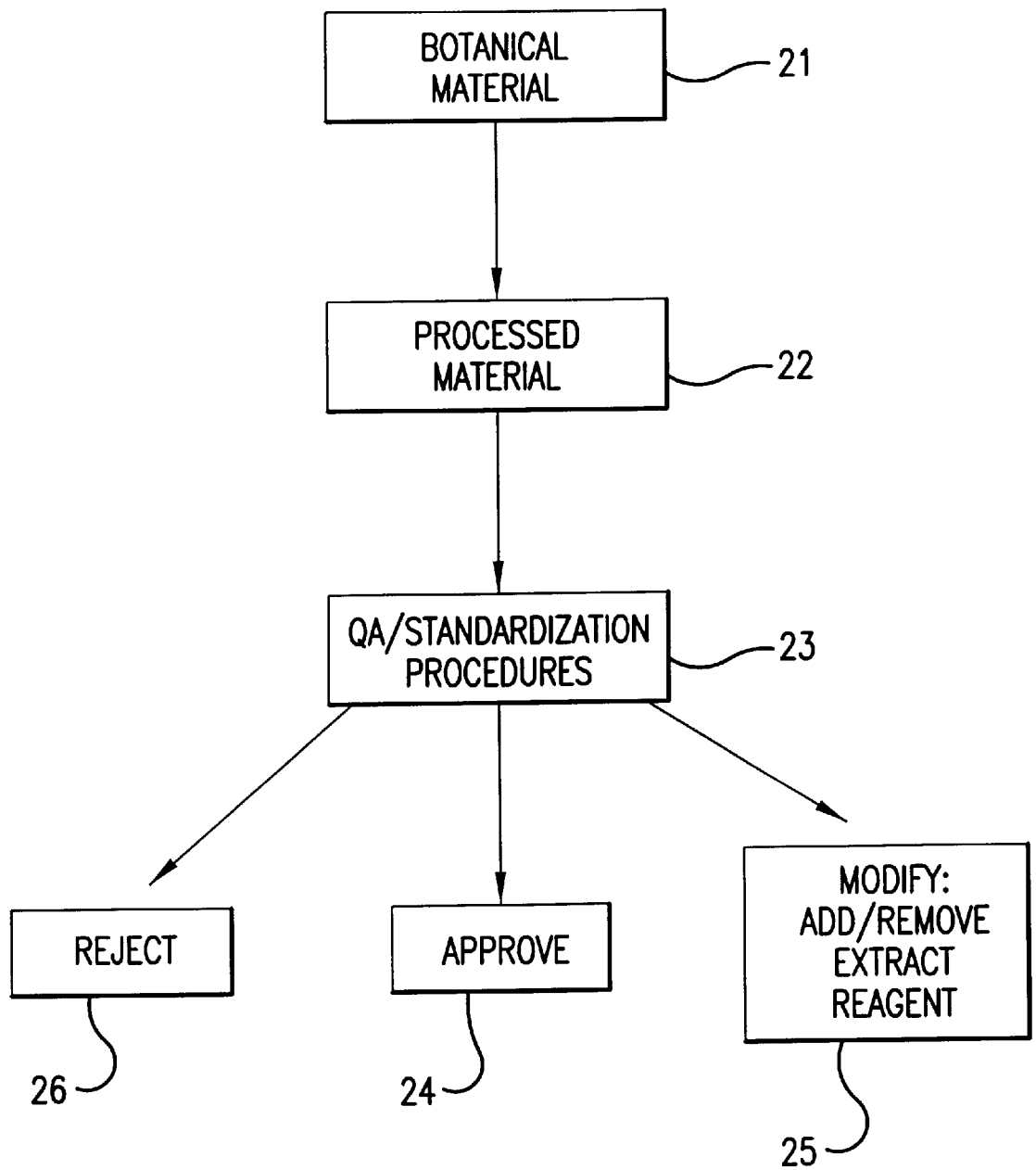
FIG. 2 is a schematic representation of a procedure in accordance with the present invention which is used to process botanical materials into pharmaceutical grade drugs.

An exemplary procedure for producing pharmaceutical grade botanicals in accordance with the present invention is shown schematically in FIG. 2. The botanical of interest 21 is first processed by extraction, powdering or other manufacturing process to form a processed botanical material 22. A sample of the processed material 22 is then analyzed to establish whether or not it matches the fingerprint requirements established during the standardization procedure of FIG. 1. This quality assurance or standardization procedure is depicted at 23 in FIG. 2. If the processed material meets the previously established fingerprint requirements for the particular material, then it is approved as being of pharmaceutical grade as represented by step 24. If the material is close, but does not quite match the standard fingerprint, then it is modified as required to match the fingerprint standards (step 25). The modification of the processed material to meet fingerprint standards may be done by a variety of ways. The methods of further processing botanicals may including additional extraction of the botanical, selective extraction, selective processing, recombination of batches (e.g. mixing high and low dose batches to prepare the pharmaceutical grade material) or the addition of various compounds, as required. If the botanical is substantially outside the fingerprint ranges for both bioactivity markers and quantitative markers, then the batch is rejected (step 26).

In one embodiment, the quality assurance standardization step 23 used to determine if a given botanical is pharmaceutical grade involves obtaining a uniform sample, preferably a homogeneous sample, or aliquot of the botanical which is to be tested. The sample should include the active components which contribute to the observed biological activity of the material and produce the bioactivity and/or chemical fingerprint of the previously determined standard. The sample will also include one or more inactive components. Inactive components are those which may not have a direct measurable biological activity. Inactive components include the following categories: components with activity so low that they do not account for a substantial portion of the activity; components whose presence indicates the presence of other bioactive components and can act as proxy markers for these components; inactive components that are chemically or biologically inactive in the relevant assays. The sample is preferably only a small aliquot of the botanical material being tested. Accordingly, it is important that a uniform sample, preferably a homogeneous sample, be obtained which is representative of the entire batch of material.

Figure 3:
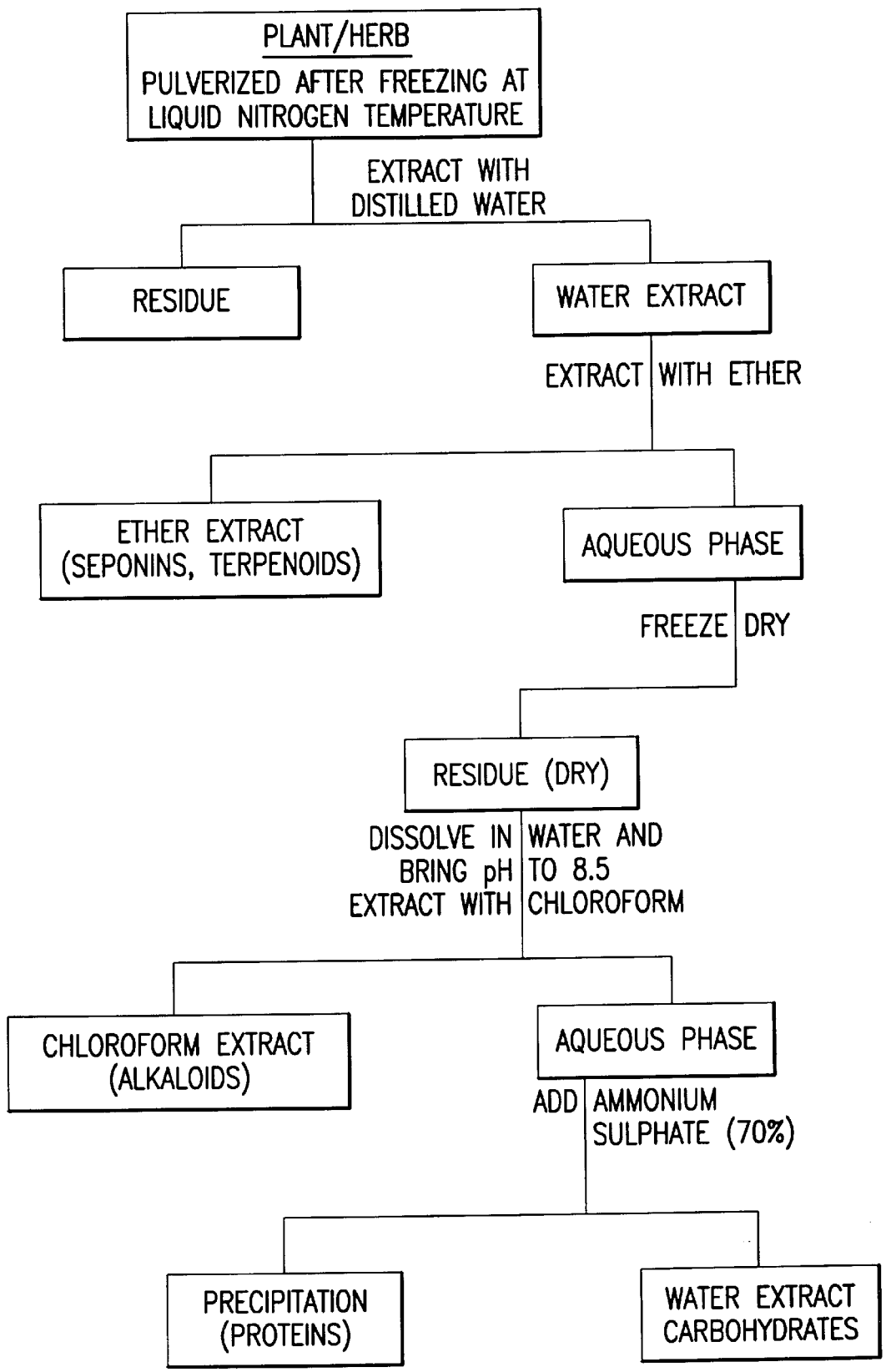
FIG. 3 is a schematic representation of a procedure for isolating different classes of biologically active components.

A more detailed schematic is shown in FIG. 3 showing the initial separation of the different components present in an aqueous extract of a botanical. Sequential extraction and precipitation are used to isolate the active components in either the aqueous or the organic phase. The scheme in FIG. 3 is particularly well suited for separating the classes of water-soluble active components from a botanical such as mistletoe.

An exemplary general method for separating plants into major classes of chemical components is set forth schematically in FIG. 3. Primarily fresh plants (including leaves, roots, flowers, berries and stems) should be used, although dried materials may also be utilized. Specific plant parts, such as the leaves, flowers, stems or root may be used if desired.

In this method the specific part or whole plant may be frozen at liquid nitrogen temperature. This facilitates grinding and also preserves the integrity and potency of the active components.

The pulverized powder is extracted with distilled water repeatedly. If desired, the extraction may be carried out with hot water, alcohol, other organic solvents, aqueous alcohol, dilute acetic acid or any combination thereof. The actual temperature chosen is preferably close to or at the boiling temperature of water. It is preferred that the overall bioactivity of the extract be initially determined. The combined extracts are subjected to a specific bioassay, e.g., a test for inhibiting the growth of bacteria in Petri dishes if the drug is to be used as an antibacterial. Alternatively, tests against cell cultures of cancer cells are conducted preferably if the drug is intended for use as an anticancer agent. From these data, bioactivity units contained in an extract per ml are calculated (bioactivity units are defined as the dilution number of this extract needed to inhibit 50% growth of bacterium or cancer cell in test system). Similarly bioactivity units for a stimulatory effect, e.g., immunostimulation can be calculated.

For establishing a pharmaceutical fingerprint (PharmaPrint®) in accordance with the present invention, the plant is extracted according to the procedure as set forth in FIG. 3 to separate it into major components (e.g. saponins, terpenoids, lipids, alkaloids, nucleic acids, proteins and carbohydrates). Each separated group of components is tested for bioactivity as needed. This may point to activity (e.g. in protein and alkaloid fractions as in *Viscum album*). The active class or classes of compounds are further separated into individual components by affinity chromatography, high performance liquid chromatography, gas chromatography or other chromatography. The components with major contribution towards biological activity are quantified on the basis of weight and specific bioactivity units. These components provide the fingerprint to establish the pharmaceutical requirements for the original herbal extract. The bioactivity units per ml of the pharmaceutical grade extract provide a way to establish exact dosage for clinical studies.

Once the sample is separated into individual marker fractions, and at least one having at least one active component, each fraction is analyzed to determine the amount of active component therein and provide a quantitative fingerprint of the sample. The quantitation of each fraction can be achieved using any of the known quantitative analysis methods. Exemplary quantitation methods include gravimetric analysis, spectral analysis or the use of quantitative detectors, such as those used in gas chromatography or high performance liquid chromatography and other separation systems. Other suitable quantitative analytical methods include analysis by enzymatic, radiometric, calorimetric, elemental analysis spectrophotometric, fluorescent or phosphorescent methods and antibody assays such as enzyme linked immunosorbant assay (ELISA) or radioimmunoassay (RIA).

In one embodiment, the results of the quantitative analysis of each fraction are used to prepare a quantitative fingerprint of the sample. The fingerprint is composed of the quantity of component in each of the marker fractions and the identity of the component. This quantitative fingerprint is then compared to the known standard fingerprint which has been established (FIG. 1) in order for the material to be considered as pharmaceutical grade. If the quantitative fingerprint of the sample falls within the range of quantities set forth for the pharmaceutical grade fingerprint, then the material may be identified as being of pharmaceutical grade.

As a further part of the quality assurance assay, the individual marker fractions may be subjected to biological assays. The biological assays which are used to test the various fractions are the same as those used for the standard fingerprint and will also depend upon the particular clinical use intended for the material.

The bioactivity fingerprint generated for the material is compared to the standard bioactivity fingerprint which has been established in order for the material to be considered as pharmaceutical grade. If the bioactivity fingerprint of the sample falls within the range of bioactivities set forth for the pharmaceutical grade fingerprint, then the material is identified as, and approved as, being of pharmaceutical grade.

5.1.2. Alternative Methods of Developing a Pharmaprint®

The method of developing a PharmaPrint® for a botanical when the putative active components are not known also begins with a literature review. It involves reviewing any chemical literature, biological literature, published bioassays or clinical data available for the botanical, or related botanicals, or for botanicals with related activities. Based on the disease state, a series of relevant bioassays is chosen. The activity of the total sample or extract is analyzed using bioassays. Those bioassays that show activity are then used to analyze fractions of the botanical for which the putative active components are not yet known. The fractionation is based on the usual methods, e.g., separation by dielectric constant, biological affinity, polarity, size, solubility or absorptive power. The fractions are then analyzed to determine which fraction is responsible for the activity. Assuming activity is found, each active fraction is refractionated to isolate the individual putative active components, i.e., pure chemical compounds. Based on knowing the individual chemical compounds and knowing their quantitative biological activity, a quantitative potency curve may be drawn and the 50% inhibitory concentration ($IC_{50}$) for each individual chemical component may be determined. If the putative active components are agonists, then other parameters (binding, activation, response) may be needed. In the general case, the bioassay will consist of appropriate tests of the stimulatory or inhibitory effects of the constituents, fractions or entire extract, followed by an appropriate quantitative evaluation of those effects. For the most likely (or typical) assays in which a standard (or radiolabelled) agonist or antagonist causes a measurable effect, inhibition and/or stimulation by the subject material may be assessed and expressed typically via the determination of an $IC_{50}$, $EC_{50}$, etc. value, or other suitable measure (e.g., $K_i$, $K_d$, $K_m$, etc). The activities of individual putative active components are then totalled and that summation is compared to the activity in the unfractionated botanical sample. If these components account for a substantial portion of the activity, then one has an initial fingerprint of "active components" for the botanical where the active components were not known.

5.1.3 Additional Variations on the Method of Developing a Pharmaprint®

The general method outlined above for PharmaPrinting™ a botanical whose putative active components are not known has several variations should complications arise in the course of the analysis. One variation occurs when the summation of individual components do not account for a substantial portion of the biological activity of the botanical. At this point there are several likely reasons for the reduced activity of the individual components, one, decomposition or degradation of active components or, two, a synergistic effect. In another possible scenario there may be no significant or greatly lessened activity seen from any of the fractions, but the whole botanical or extract shows activity in the bioassay. Nonspecific matrix effects may also lessen the total extract activity, when compared to standards.

To determine if the active components are decomposing in the course of the assay is relatively simple. One merely recombines all of the fractions and compares the activity of the recombined fractions with the activity of the crude material. If substantial activity has been lost, then the problem is probably decomposition. To determine which active components may be decomposing, the chromatographic analysis of the crude botanical is compared with that of the recombined fractions. Peaks that are missing or are reduced in size indicate that components may be decomposing. To overcome decomposition many methods exist. Typically, milder extraction/fractionation methods such as liquid-liquid chromatography (counter-current chromatography) or supercritical carbon dioxide extraction or chromatography may be used.

Another explanation for the activity of the individual fractions not accounting for a substantial portion of the expected total activity is a synergistic effect between one or more active components with each other, or inactive components. To determine that a synergistic effect is taking place, pair-wise recombined fractions need to be analyzed. If the combined fractions show more activity than the individual fractions, two or more individual components in the fractions may be acting synergistically. For example, one may have three fractions, each alone responsible for 10% of the bioactivity (i.e., their uncombined additive bioactivity is 30%) but combined responsible for 100% of the activity. In that case the fractions are acting synergistically. By repeated pair-wise recombination of fractions or looking at larger fractions, any synergistic activity will be discovered. Once two fractions show synergy, they are then refractionated as above, and pairs of individual fractions or pairs of isolated components are studied to find the individual components that act synergistically. Three way comparisons of individual components or fractions may also be studied.

What if the fractions have no activity in the bioassay in which the botanical shows activity? Here, the explanations include decomposition, synergy, or many active components such that no individual fraction shows activity. The first step would be to fractionate each initial fraction and see if active components appear in the bioassay. It that does not succeed, the fractions should be recombined and assayed to determine if decomposition of the actives is taking place. If decomposition is taking place, the appropriate measures as described above should be taken. If there is no decomposition, then alternative methods of fractionation should be tried. Eventually, large enough or appropriately sized or selected fractions will show activity. If synergy is a suspected problem, then proceed as in the synergy section described above.

5.2. Methods of Processing and Extracting Bontanical Materials

The botanical material may be processed to form an aqueous or organic extract of the whole plant or a selected part of the plant. The botanical material can also be processed in whole or part to form a powder. Many of the botanicals of interest are commercially available as powders, aqueous extracts, organic extracts or oils. In one embodiment, extracts of the plant material are preferred because they are easier to dissolve in liquid pharmaceutical carriers. However, powdered plant materials are well-suited for many applications where the drug is administered in solid form, e.g., tablets or capsules. Such methods are well known to those of skill in the art. Furthermore, many of the plant materials and/or extracts are available commercially. As examples of the processing and extracting of botanicals the following examples are provided. Additional examples are provided in the detailed description.

For a typical root, it may be sliced, frozen or pulverized. If powdered it is then shaken with an appropriate solvent and filtered (Tanabe et al., 1991, *Shoyakugaku Zassi*, 45(4) :316–320). Alternatively, the following methods are used: the root is homogenized, acetone extracted and filtered; the botanical may be steam distilled to obtain essential oils and the distillate dissolved in acetone-water or appropriate solvent; or the cut rhizomes are frozen and/or freeze-dried and the resulting powder acetone-water extracted (Tanabe et al., 1991, *Shoyakugaku Zassi* 45(4):321–326). Another method of processing botanicals is aqueous extraction with 100° C. water (Yamahara et al., 1985, *J. Ethnopharmacology* 13:217–225). The initial solvent extract from the methods above may be further extracted using liquid/liquid extraction with an appropriate solvent. The botanical may be extracted in two steps using polar and non-polar solvents respectively. The solvents are then evaporated and the fractions combined (Nagabhusan et al., 1987, *Cancer Let.* 36:221–233). Botanicals may also be processed as a paste or powder which may be cooked (Zhang et al., 1994, *J. of Food Science* 59(6) :1338–1343).

A variety of solvents may be used to extract the dried botanicals, for example acetone, acetonitrile, dichloromethane, ethyl acetate, ethanol, hexane, isopropanol, methanol, other alcohols, and supercritical carbon dioxide (Sipro et al., 1990, *Int. J. of Food Science and Technology* 25:566–575 and references therein).

For other botanicals such as Saw Palmetto, the medicinal products are the seed oil or dried berries. In a typical preparation, a hexane or supercritical carbon dioxide extract is prepared. Many Saw Palmetto preparations are commercially available, for example Permixon™ or Talso™. For an example of supercritical carbon dioxide extraction of a botanical, see Indena, European Patent No. 0 250 953 B1. Alternatively, the botanical may be crushed and extracted with an appropriate solvent (90%) in a soxhlet (Elghamry et al., 1969, *Experientia* 25(8):828–829). The botanical may also be ethanol extracted (Weisser et al., 1996, *The Prostate* 28:300–306).

The dried material may be prepared in a variety of ways including freeze-drying, drying via microwave, cooling with liquid nitrogen and pulverizing; drying at 70° C. under vacuum for a duration of 10 hours; or air-drying in the shade, or with forced heated air (List and Schmidt, *Hagers Handbuch der Pharmazeutischen Praxis*, Springer-Verlag: New York, 1993, 1973–79; Araya et al., 1981, *Journal of Comparative Pathology*, 135–141). Teas, dilute aqueous extracts, also known as infusions, may be made in 60–100° C. water (Nosel and Schilcher, 1990). Decoctions may also be utilized. Extraction is more efficient when the particle size is less than 0.25 mm (List and Schmidt, *Phytopharmaceutical Technology*, CRC Press: Boca Raton, Fla., 1989).

Various guidelines are available for preparing oil extracts of botanicals. The botanical may be digested (macerated) in oil at 45° C. for 10 days, while others recommend 70° C. for 12–24 hours (Hobbs, 1989, *HerbalGram* 18/19:24–33; Smith et al., *Quality Validation Laboratory-Herb Pharm*: Williams, Oreg., 1996). In St. John's Wort for example, exposing the preparation to sunlight during the extraction process has been reported to result in a four-fold increase in flavonoid content calculated as quercetin (Maisenbacher and Kovar, 1992). Additionally, for St. John's Wort, two-fold increases of hypericin have been reported in oil preparations in which the material has been further extracted with alcohol, and mixed with the oil (Georgiev et al., 1983, *Nauchni Tr.-Vissh Inst. Plovid.* 30:175–183).

Alternatively an alcohol-water preparation may be prepared of the botanical (Dyukova, 1985, *Farmitsiya* 34:71–72; Georgiev et al., 1985, *Nauchni Tr.-Vissh Inst. Plovid.* 32:257–263; Wagner and Bladt, 1994, Kowalewski et al., 1981, *Herba Pol.* 27:295–302). According to Hagers Handbuch a tincture of a botanical, such as St. John's Wort, may be prepared by using drug or freezing ethanol soaked botanical materials, and filtering and preserving in dark bottles (List and Hörhammer, 1993).

Some botanicals, such as St. John's Wort, are both temperature and light sensitive. For this type of botanical the material should be dry packed with a refrigerant or shipped under refrigeration and protected from light and air. In St. John's Wort, hypericin content has been shown to drop significantly in powdered extract, tablet and juice preparations when stored at temperatures of 60° C.–140° C. for more than six weeks. Dry extracts stored at 20° C. were found to remain stable for at least one year (Adamski et al., 1971, *Farm. Pol.* 27:237–241; Benigni et al. *Hypericum. Plante Medicinali: Chimica, Farmacologia e Terapia*, Milano: Inverni & Della Beffa; 1971). Other St. John's Wort constituents, hyperforin and adhyperforin found in oil preparations are highly unstable, especially when exposed to light, and can degrade in as little as 14 days (Meisenbacher et al., 1992, *Planta Med.*, 351–354). Stability (in absence of air) was increased to six months in a preparation extracted with ethanol. Similarly, up to four xanthones and several flavonoids including quercetin and I3', II8-biapigenin have been detected suggesting these may be among the active constituents in external preparations (Bystrov et al., 1975, *Tetrahedron Letters* 32:2791–2794).

5.2.1 Liquid Extracts of Plant Material and Powered Plant Materials

One common form of liquid extract of botanical material are a "tea". A tea may be prepared through processes of infusion or decoction. Teas are generally an effective means to extract water soluble components from dried or fresh botanicals.

Another common form of liquid botanical extract is a tincture. A botanical tincture is typically an alcoholic or hydroalcoholic solution prepared from a fresh or dried botanical. It is usually prepared through a process of percolation or maceration.

Tinctures of potent botanicals, and homeopathic mother tinctures, may represent 10 g of botanical (dry weight) in 100 ml of tincture. Common botanicals have 20 g of botanical represented in 100 ml of tincture. The respective ratios of dried botanical to solvent for these preparations are 1:10 and 1:5, respectively. While these concentrations have been officially recognized by the U.S. National Formulary it has become common for tinctures to be prepared in 1:4, and other concentrations.

As compared to crude botanical extracts, tinctures may have a reduced microbial load and longer shelf life. This is largely due to the presence of alcohol at 20% or greater concentrations in the extract. Occasionally liquid extracts are made with glycerin and water as the solvent. These glycerites usually need to have at least 50% glycerin present to inhibit microbial contamination. Glycerites may also be prepared from tinctures by evaporating off alcohol and "back adding" glycerin in its place.

Another type of liquid extract is a "fluid extract". Fluid extracts are liquid preparations of botanicals that represent the medicinal properties of 1 g of dried botanical in 1 ml of extract. Official versions are made by the percolation process according to official monographs which determine the solvent to be used.

Liquid extracts that are concentrated, usually through evaporation of the solvent, may form extracts that are oily, semi-solid or solid in nature.

Dry powdered extracts may be prepared by the absorption of liquid extracts, oils, or semi-solids onto suitable carriers before solvent removal. Alternatively, dry powdered extracts may be prepared by direct removal of solvent from a liquid extract to provide a solid extract which can be powdered.

5.3 Separation of Fractions

Once the sample extract has been prepared and/or alternatively purchased as a commercially available extract, a portion needs to be subjected to fractional analysis. If the fingerprint has already been established, the sample or aliquot is separated into the same plurality of marker fractions which are present in the standard fingerprint. Each of the marker fractions will include one or more of the active or inactive components. The marker fractions are established on an individual basis for each botanical material being tested. For some materials only a few marker fractions are required. For other more complex materials, there may be numerous marker fractions. For example in mistletoe, *Viscum album* L. protein extract, the preferred protein marker fractions are those fractions which are separated based on the sugar binding affinity of the fraction. However, different parameters for identifying and separating the materials into the marker fractions may be established based upon the types of components present in the botanical material. Separation of the sample into the marker fractions may be accomplished by any of the conventional separation techniques including liquid chromatography and extraction procedures. The same procedures which were used to establish the standard fingerprints should be used. Since the various fractions may be tested for biological activity, it is preferred that non-destructive separation techniques be utilized. Liquid column chromatography is a useful separation technique with affinity chromatography based on the specific binding ability of the compounds (e.g., carbohydrates and target enzymes) being particularly used.

After the fractionation, the solvent is removed and the material is dissolved in an appropriate medium for the bioassays. Examples of appropriate media include DMSO, ethanol, various detergents, water and an appropriate buffer. The choice of solvent will depend on the chemical nature of the component being analyzed and the compatibility with the assay system.

5.4 Establishment of Appropriate Bioassays

Exemplary biological assays may include any cell proliferation assays, such as the measurement of L 1210 cell inhibition, immune activity or inhibition of critical enzyme which relates to specific diseases. Examples of other transformed cell lines which can be used for bioassays include HDLM-3 Hodgkin's lymphoma and Raji Burkitt's lymphoma, hepatoma cell line, primary or established cultures of human/animal cell lines which carry specific cell receptors or enzymes.

The results of the biological assays are used to prepare a bioactivity fingerprinting of the material. The fingerprint can be as simple as an assay of two selected marker fractions. Conversely, the fingerprint can include numerous different bioassays conducted on numerous different fractions. The same assay may be conducted on different marker fractions. Also, different assays may be conducted on the same marker fraction. The combination of bioassays will depend upon the complexity of the given botanical material and its intended clinical use. The bioassays will be the same as those conducted in establishing bioactivity fingerprint of the standard material.

5.4.1. Enzymatic and Receptor Based Assays

Enzymatic and receptor based assays are preferable in the practice of this invention. Assays are chosen either based on accepted enzymatic assays for a clinical disorder or they are chosen from relevant assays for a given clinical disorder. It is important to choose appropriate bioassay that may be validated. Ideally, a bioassay should be rugged, that is reproducible over time and show a quantitative dose response over a wide concentration range. An issue faced with a botanical for which the active components are not known is the choice of a relevant bioassay. Here, the human therapeutic use will serve as a guide to pick assays known in the art based on possible mechanisms of action. The echanism of action should be consistent with a clinically relevant endpoint. There are a wide array of clinically relevant assays based on enzymatic activity, receptor binding activity, cell culture activity, activity against tissues and whole animal in vivo activity.

This section will address enzymatic and receptor binding assays. There are many books on enzymatic or receptor assays, for example, *Methods in Enzymology* by Academic Press or Boyers, *The Enzymes. Bioactive Natural Products, Detection, Isolation, and Structural Determination*, S. M. Colegate and R. J. Molyneux, CRC Press (1993), also discusses specific bioassays. *Methods in Cellular Immunology*, R. Rafael Fernandez-Botran and V. Vetvicka, CRC Press (1995) describes assays from immune cell activation and cytokine receptor assays. "Screening Microbial Metabolites for New Drugs-Theoretical and Practical Considerations" describes additional methods of finding pharmaceutically relevant bioassays (Yarbrough et al. (1993) *J. Antibiotics* 46(4):536–544). There are also many commercial contract research vendors, including Panlabs, Paracelsian and NovaScreen. For example, for a botanical useful for treating neurological disorders, the array of bioassays might include adrenergic receptors, cholinergic receptors, dopamine receptors, GABA receptors, glutamate receptors, monoamine oxidase, nitric oxide synthetase, opiate receptors, or serotonin receptors. For cardiovascular disorders the array of assays may include adenosine A, agonism and antagonism; adrenergic $\alpha_1$, $\alpha_2$, $\beta_1$ agonism and antagonism; angiotensin I inhibition; platelet aggregation; calcium channel blockade; ileum contractile response; cardiac arrhythmia; cardiac inotropy; blood pressure; heart rate; chronotropy; contractility; hypoxia, hypobaric; hypoxia, KCN; portal vein, potassium depolarized; portal vein, spontaneously activated; or thromboxane $A_2$, platelet aggregation. For metabolic disorders the following bioassays may be used: cholesterol, serum HDL, serum total; serum HDL/cholesterol ratio; HDL/LDL ratios; glucose, serum— glucose loaded; or renal function, kaluresis, saluresis, and urine volume change. For allergy/inflammation disorders the following bioassays may be used: allergy, Arthurs reaction, passive cutaneous anaphylaxis; bradykinin $B_2$; contractility, tracheal; histamine $H_1$ antagonism; inflammation, carrageenan affects on macrophage migration; leukotriene $D_4$ antagonism; neurokinin $NK_1$ antagonism; or platelet activating factor, platelet aggregation or induction of biosynthesis of important inflammatory mediators (e.g. interleukins IL-1, IL-6, tumor necrosis factor or arachidonic acid). For gastrointestinal disorders the following bioassays may be used: cholecystokinin $CCK_A$ antagonism; cholinergic antagonism, peripheral; gastric acidity, pentagastrin; gastric ulcers, ethanol; ileum electrical stimulation modulation; ileum electrical stimulation spasm or serotonin $5-HT_3$ antagonism. For antimicrobial, antifungal, or antitrichomonal disorders the following are used: *Candida albicans; Escherichia coli; Klebsiella pneumoniae; Mycobacterium ranae; Proteus vulgaris; Pseudomonas aeruginosa; Staphylococcus aureus*, methicillin resistant; *Trichomonas foetus*; or *Trichophyton mentagrophytes*. For other indications, one of skill in the art would be able to choose a relevant list of bioassays.

Specific examples of assays based on enzymes or receptors include the following: acetyl cholinesterase; aldol-reductase; angiotensin converting enzyme (ACE); adrenergic $\alpha$, $\beta$, rat androgen receptor; CNS receptors; cyclooxygenase 1 or 2 (Cox 1, Cox 2); DNA repair enzymes; dopamine receptors; endocrine bioassays, estrogen receptors; fibrinogenase; GABA A or GABA B; $\beta$-glucuronidase; lipoxygenases, e.g., 5-lipoxygenase; monoamine oxidases (MAO-A, MAO-B); phospholipase $A_2$, platelet activating factor (PAF); potassium channel assays; prostacyclin cyclin; prostaglandin synthetase; serotonin assays, e.g., 5-HT activity or other serotonin receptor subtypes; serotonin re-uptake activity; steroid/thyroid superfamily receptors; thromboxane synthesis activity. Specific enzymatic assays are available from a variety of sources including Panlabs™ Inc (Bothell, Wash.) and NovaScreen™ (Baltimore, Md.). Additional assays include:

ATPase inhibition, benzopyrene hydroxylase inhibition, HMG-CoA reductase inhibition, phosphodiesterase inhibition, protease inhibition, protein biosynthesis inhibition, tyrosine hydroxylase and kinase inhibition, testosterone-5$\alpha$-reductase and cytokine receptor assays.

5.4.2 Cell Culture and Other Assays

In addition to the enzymatic and receptor assays, there are also other biological assays. Preferably, these assays are performed in cell culture but may be performed on the whole organism. Cell culture assays include activity in cultured hepatocytes and hepatomas (for effect on cholesterol levels, LDL-cholesterol receptor levels and ratio of LDL/HDL cholesterol); anti-cancer activity against L 1210, HeLa or MCF-7 cells; modulating receptor levels in PC12 human neuroblastoma cells; modulation of primary cell culture activity of luteinizing hormone (LH), follicle stimulating hormone (FSH) or prolactin; $Ca^{2+}$ influx to mast cells; cell culture assays for phagocytosis, lymphocyte activity or TNF release; platelet aggregation activity or activity against HDLM-3 Hodgkin's lymphoma and Raji Burkitt's lymphoma cells, antimitotic activity, antiviral activity in infected cells, antibacterial activity (bacterial cell culture) and antifungal activity. Tissue or whole animal assays may also be used including anti-inflammatory mouse ear dermatitis, rat paw swelling; muscle contractility assays; passive cutaneous anaphylaxis; vasodilation assays; or whole animal carbon clearance tests. These assays are available from a variety of sources including Panlabs™ Inc. (Bothell, Wash.).

5.4.3. Anticancer Activity

The anticancer effects of drug can be studied in a variety of cell culture systems; these include mouse leukemias, L 1210, P388, L1578Y etc. Tumor cell lines of human origin like KB, and HeLa have also been used. In a typical assay tumor cells are grown in an appropriate cell culture media like RPMI-1640 containing 10% fetal calf serum. The logarithmically growing cells are treated with different concentrations of test material for 14–72 hours depending upon cell cycle time of the cell line. At the end of the incubation the cell growth is estimated by counting the cell number in untreated and treated groups. The cell viability can be ascertained by trypan blue exclusion test or by reduction of tetrazolium dyes by mitochondrial dehydrogenase. The ability of a drug to inhibit cell growth in culture may suggest its possible anticancer effects. These effects can be verified in animals bearing tumors, which are models for human disease (Khwaja, T. A., et al. (1986) *Oncology,* 43 (Suppl. 1): 42–50).

The most economical way to evaluate the anticancer effects of an agent is to study its effects on the growth of tumor cells in minimum essential medium (MEM) containing 10% fetal calf serum. The drug-exposed cells (in duplicates) are incubated in a humidified $CO_2$ incubator at 37° C. for 2–4 days, depending upon the population-doubling time of the tumor cells. At the end of the incubation period the cells are counted and the degree of cell growth inhibition is calculated from a comparison with untreated controlled cells grown under identical conditions. The type of cell lines used have varied from laboratory to laboratory depending upon individual needs. The National Cancer Institute (NCI) in the United States recommends the use of KB cells (a human nasopharyngeal carcinoma) for the evaluation of anticancer drugs in vitro. The cell growth inhibition is determined by estimating the protein content (Lowry's method) of the drug-treated and untreated controls. NCI has also recommended the use of suspension culture of mouse leukemia P388 for the evaluation of anticancer potential of plant extracts and related natural products.

Mouse leukemia L1210 cells, cultured in microtiter plates are routinely used for in vitro assays for anticancer activity. The cell population-doubling time of leukemia L1210 is 10–11 h and a drug exposure of 48 h (3–4 generations of logarithmic growth) is used for the evaluation of its antitumor activity. For growth inhibition studies all stock solutions and dilutions are made with sterile 0.9% NaCl solution. The cell cultures are seeded at $2–5\times10^4$ cells/ml in duplicates for each inhibitor concentration in a microtiter place (0.18 ml/well). The inhibitors are added in 0.02 ml volume to achieve 1:10 dilutions in each case. The covered microtiter plate is incubated for 48 h in a humidified $CO_2$ incubator containing 5% $CO^2$ in air. At the end of the incubation period aliquots of each well are added to a measured volume of isotonic saline and counted in an electronic cell counter. The cell viability is determined by trypan blue exclusion. The results are calculated by plotting percent cell growth inhibition (as compared to cell density of the saline-treated controls) versus log of drug concentration and expressed as the concentration which caused 50% inhibition in cell growth ($IC_{50}$) as determined from the graph.

The cytotoxic effects of a drug on a tumor cell line may also be evaluated. However, these experiments require longer periods of time to study and are more expensive. In these studies drug-treated cells are washed free of drug and then plated in soft agar or an appropriate medium and the cellular viability is estimated by the ability of the surviving cells to multiply and form microscopic colonies. The number of cellular colonies obtained with certain drug concentrations is compared with those obtained from untreated controls to evaluate cell kill or cytotoxic activity. In studies with mistletoe extract we have used loosely adherent cultures of EMT-6 cells (a mouse mammary adenocarcinoma). These cells are grown in Eagle's MEM (F14) containing 10% dialyzed fetal calf serum and antibiotics. The cell suspension is spun and the pellet suspended in Spinner's medium supplemented with 10% dialyzed fetal calf serum (70 cells/ml), plated in plastic Petri dishes and incubated for 2 h to permit cells to attach. At this time cells are exposed to various concentrations of extract for 2–24 h. Then, the medium is removed and replaced with drug-free medium and the dishes incubated for 5–7 days. The colonies are stained with methylene blue (0.33% in 0.01% KOH) and counted with an automatic colony counter. The plating efficiency of EMT-6 cells is 46%. (Khwaja et al., 1986, *Oncology,* 43(Supp. 1):42–50).

5.4.4. Antiviral Activity

The antiviral activity of different drugs can be ascertained in cell culture of human cell lines like HeLa or H9 lymphoma cells. These cells are infected with virus and the virus is allowed to propagate in cell cultures. The ability of virus to produce cell lysis or cytopathic effects is taken as the end point. For example, HIV infection of H9 cells results in production of multinucleated cells. These cytopathic effects, if reduced or eliminated by certain concentrations of the drug, indicates its potential as an anti-HIV agent. These results can be validated by estimation of viral enzyme in the cell cultures, e.g., by studying the amount of the expression of viral reverse transcriptase. A decreased expression of the viral enzyme would support antiviral effect of the drug treatment (Khwaja, T. A. U.S. Pat. No. 5,565,200; J. Levy et al. 1984, *Science* 225:840).

5.5. Analytical Methods for Analyzing Chemical Components

There are many methods to separate and analyze individual chemical components including gas chromatography (GC), mass spectroscopy (MS), GC-MS, high performance liquid chromatography (HPLC), HPLC-MS, thin layer chromatography (TLC), high performance TLC (HPTLC) gel chromatography and reverse phase chromatography (RPC). These chromatographic methods may be performed either on an analytical scale or a preparative scale. To determine the actual chemical structure of unknown components, nuclear magnetic resonance (NMR) and mass spectrum fragmentation analysis are typically used.

The determination of the type of chromatography will depend on the chemical components most likely responsible for the bioactivity. For example if the bioactivity is likely due to fatty acids, the fatty acids are esterified and the esters analyzed on a GC. For organic compounds with alcohol groups, they are modified to prepare ethers, silyl derivatives or other less polar functional groups. These derivatives are then suitable for analysis by GC (Steinke et al., 1993, *Planta Med.* 59:155–160; Breu et al., 1992, *Arzneim.-Forsch/Drug Res.* 42(1):547–551). If the activity is most likely due to flavonoids, HPLC is the method of choice. Reverse-phase HPLC (RP-HPLC) has been used to analyze flavonoids from a variety of botanicals, specifically hawthorn, passion flower, chamomile, ginkgo (Pietta et al., 1989, *Chromatographia* 27(9/10):509–512). Plant constituents have been quantitatively determined by TLC (Vanhaelen and Vanhaelen-Fastre, 1983, *J. Chromatography* 281:263–271) as well as MS-analysis for garlic. CRC Handbooks of Chromatography on "Analysis of Lipids", K. D. Mukherjee, "Analysis and Characterization of Steroids", H. Lamparczyk, J. Sherma, and "High-Performance Liquid Chromatography of Peptides and Proteins", C. T. Mant and R. S. Hodges, are available and describe columns and solvent systems.

5.6. Analysis of Fractions

In an alternative embodiment, rather than base the pharmaceutical fingerprint (PharmaPrint®) on discrete chemical components of known bioactivity, one may also establish the PharmaPrint® using defined fractions or classes of compounds. Some chemical constituents in botanicals form such a complex mixture of closely-related components that, from a practical point of view, it is desirable to base the PharmaPrint® on fractions or classes of components rather than on individual components. Examples of these types of components are lectins (sugar-binding proteins) or glycoproteins as well as the silymarins in milk thistle. There are many examples of fractional analysis (*Gel Filtration Principles and Methods Pharmacia Biotech*, Rahms i Lund: Sweden; Utsumi et al., 1987, *J. Biochem.* 101:1199–1208).

5.7. Methods of Use of Pharmaprinted™ Materials

After the botanical material has an established fingerprint, individual samples are then analyzed to determine if they fall within the accepted standards. Once the sample has been approved it is suitable for a variety of diseases relevant to humans and animals. Such materials are useful in clinical trials so as to provide materials of consistent quality and precise dosage ose formulations for trials. The PharmaPrinted™ material is also useful for toxicological tests in animals where once again the consistency of the material is useful for quantitative toxicological analysis. In many cases it would be of use as a reference material for analytical or biological use.

The PharmaPrinted™ botanical materials are useful for any disease state for which a botanical drug is associated. See for example Leung and Foster, 1996 and *Herbal Drugs and PhytoPharmaceuticals*, 1994. More specific examples of disease states or therapeutic indications include AIDS, adaptogen, mild-to-moderate depression, anti-arthritic, anti-cancer, anti-diarrhetic, anti-helmenthic, anti-inflammatory, anti-nausea via GI, anti-rheumatic, anti-spasmodic, anti-ulcer, angina, antibacterial, antimutagenic, antioxidant, antiviral, arteriosclerosis, arthritis, asthma, blood pressure, benign prostatic hyperplasty (BPH), bronchial asthma, bronchitis, calmative, cough, cerebral circulatory disturbances, cholesterol lowering, cirrhosis, dermatological anti-inflammatory, diabetes, diuretic, drastic cathartic, dysmenorrhea, dyspepsia, emphysema, environmental stress, expectorant, free radical scavenger, GI distress, hemorrhoids, hepatitis, hepatoprotective, hypertension, hyperlipidemia, hyperprolactinemia, immunomodulatory activity, increase fibrinolysis, resistance to bacterial infection, inflammation, insomnia, lactation, liver protection, longevity, menstrual cycle regulation, migraine, muscle pain, osteoarthritis, pain, peripheral vascular disease, platelet aggregation, PMS, promote menstrual flow, prostatic disorders, reduce triglycerides, relieve menstrual pain, respiratory tract infections (RTI), retinopathy, sinusitus, rheumatism, sedative, sleep-promoting agent, sore throat, stimulate hair growth, superficial wound healing, tinnitus, topical eczema (dermatitis), urinary tract infection (UTI), varicose veins, venous insufficiency or wound healing.

Other indications include anti-hemorrhagic, anti-microbial, anti-parasitic, anti-pyretic, cardiotonic, carminitive, cholagogue, demulcent, diaphoretic, emetic, emmenagogue, emollient, febrifuge, galactagogue, hepatic, hypnotic, laxative, nervine, pectoral, rubefacient, stimulant, tonic, vulnerary, canker sores, pyorrhea, gingivitis, gastritis, ulcers, gallstones, intermittent claudication, cold, influenza, laryngitis, headache, shingles, cystitis, kidney stones, atopic vaginitis, uterine fibroids, osteoporosis and gout.

Saw palmetto is useful for allergic and anti-inflammatory conditions, in particular, benign prostatic hypertrophy.

5.8. Pharmprint® of Saw Palmetto

5.8.1. Biological Pharmaprint®

Exemplary biological PharmaPrint® values for a saw palmetto, derived using the methods described herein, are shown in Table 4. See, infra, Section 6.4 for a detailed discussion and explanation of each of the biological assays for each of the values presented in Table 4.

Values for each bioassay are expressed on $IC_{50}$ unless otherwise indicated. Calculations for extracts and fractions are based on an assumption of an average molecular weight of 200.

TABLE 4

BIOLOGICAL PHARMAPRINT®

| Extracts | Androgen Receptor (% Inhibition) | |
|---|---|---|
| RANGE 1 | >20% Inh. @ $10^{-5}$M or 20 ± 10% | |
| Marker Compounds | | |
| $IC_{50}$ in $\mu$M | Androgen Receptor | |
| Ethyl laurate | 0.13 | |
| Ethyl linolenate | 42 | |
| β-sitosterol | 2.4 | |
| Phytol | 10 | |
| Linolenic Acid | Cyclo-oxygenase-1 | 5-Lipoxygenase |
| | 233 | 12 |

By way of example, using the values in Table 4, the PharmaPrint® may be based on the bioactivity of extract in the androgen receptor assay and one or more assays selected cyclo-oxygenase-1 or 5-lipoxygenase.

In an alternative embodiment, the PharmaPrint® may be developed based on bioactivity equal to or greater than the lower end of the range of bioactivity values such as shown in Table 4. As an illustrative example of this embodiment, the PharmaPrint® value based on the bioactivity IC50 of total extract in the >20% Inh. @ $10^{-5}$ in the androgen receptor assay.

5.8.2. Chemical Pharmaprint

PharmaPrinting saw palmetto revealed four active components illustrated below in Table 5. See, infra, Section 6.5 for a detailed discussion and explanation of the selection of the chemical compounds.

TABLE 5

CHEMICAL PHARMAPRINT

| Range (% w/w) | Broad Range | Intermediate | Narrow Range |
|---|---|---|---|
| Ethyl laurate | 0.5–25 | 1.0–15 | 2.0–8.0 |
| Ethyl linolenate | 0.01–10 | 0.015–8 | 0.02–5.0 |
| β-sitosterol | 0.01–3 | 0.05–1 | 0.1–0.5 |
| Phytol | 0.005–2 | .008–0.5 | 0.01–0.15 |
| Linolenic acid | 0.05–2.0 | 0.1–1.0 | 0.2–0.7 |
| Total fatty acids | 50–100 | 70–100 | 80–95 |

5.8.3. Conversion Ratio

PharmaPrint® values developed using dry powdered extracts of a botanical material can be converted to values relevant to dry weight of raw botanical material using the ratios illustrated in Table 6 below. Thus, to convert PharmaPrint® values based on a dry powdered extract to values relevant to a dried plant material, one would divide by the appropriate factor in Table 6.

TABLE 6

CONVERSION RATIOS

CONVERSION RATIOS

| Botanical | Ratio (powder to extract) |
|---|---|
| Saw Palmetto | 10:1 |
| St. John's wort | 5:1 |
| Valerian | 5:1 |
| Echinacea | 5:1 |
| Ginkgo | 50:1 |
| Ginseng | 5:1 |
| V. Agnus castus | 10:1 |
| Black Cohosh | 1:1 |
| Bilberry | 100.1 |
| Milk Thistle | 40:10 |

The following example is presented for purposes of illustration only and is not intended to limit the scope of the invention in any way.

6. EXAMPLE: Saw Palmetto, *Serenoa repens, Serenoa serrulata, Sabal serrulata*

6.1 Commercial Supplies/Product Names

There are many commercial suppliers of *Sabal serrulata* extracts. The following names are used: IDS 90 (Weisser et al., 1996, *The Prostate* 28:300–306); Strogen Forte, Talso™, SG290 Talso™ uno, commercially available from Sanofi Winthrop GmbH (Munich, Germany). Extracts are also available from Madaus S. A. (Köln, Germany). Permixon™ is available from Centre de Recherches P. Fabre (Castres, France). Several varieties of Permixon extract are available, including a lipophilic extract, LSESr extract, and a PA109 extract. Another product available is Prostaserene™, a purified extract of *Serenoa repens*, commercially available from Therabel Pharma™, (Belgium). Saw Palmetto is also produced by the following companies: NaturaLife, Herbal Choice, Botalia Gold, Herb Pharm, PhytoPharmica.

6.2 Fractional Analysis of Saw Palmetto

The fractionation of the contents of commercially available gel caps of Saw Palmetto was performed using normal phase flash chromatography. This method was selected as a preferable prep-chromatographic technique on the basis of observed excellent mass recovery (>90%), the separation of the selected standards (fatty acids, their esters), as well as separation of the other co-occurring components. A detailed description of the materials and methods utilized is described below.

A comprehensive search of the literature on Saw Palmetto (*Sereno repens*) indicated that phytosterols (β-sitosterol), fatty acids (palmitic, oleic, linoleic, linolenic, myristic and lauric acids), as well as their ethyl esters, are the components of Saw Palmetto with the most consistent bioactivity in a number of assays [fatty acids/esters: 5α-reductase (Weisser, 1996, supra), androgen receptors (Casarosa, 1988); phytosterols (especially β-sitosterol, although less than 10% of the activity of estradiol): estrogenic activity (Duke, 1985)].

Prep-CC Method: Approximately 5 g of the contents of a commercial gel capsule of Saw Palmetto contents were dissolved in 25 ml of $CH_2Cl_2$. The resultant extract was loaded onto a preparative flash chromatography column prepacked with $SiO_2$. The flash CC (column chromatography) conditions were as follows: column-60 μm $SiO_2$; each mobile phase volume=two column volumes; ten fractions were collected with the elution profile shown in the table below. The total recovery of 4.8 grams gave a 96% total mass balance.

Approximately 5 grams of commercially available SPB-extract (from gel capsules) were dissolved in 25 ml of methylene chloride. Flash chromatography was performed using this solution. The chromatography system consisted of 60 μm silica gel and the following eluting solvents are shown in

TABLE 6

FLASH CHROMATOGRAPHY

| Mobile Phase | Hexane | Acetone | MeOH (% V/V) |
|---|---|---|---|
| 1 | 100 | 0 | 0 |
| 2 | 90 | 10 | 0 |
| 3 | 80 | 20 | 0 |
| 4 | 70 | 30 | 0 |
| 5 | 60 | 40 | 0 |
| 6 | 50 | 50 | 0 |
| 7 | 40 | 60 | 0 |
| 8 | 30 | 70 | 0 |
| 9 | 20 | 80 | 0 |
| 10 | 0 | 0 | 100 |

The amount of dried residue recorded from each fraction of mobile phase collected was as follows 1 (~0.1 g), 2 (~2.5 g), 3 (~1.6 g), 4 (~0.1 g), 5 (~0.1 g), 6–9 (~0.0 g), and 10 (~0.5 g). The total dried residue recovered via flash chromatography was calculated to be 4.8±0.1 grams. Given the initial load of extract was 5.15 grams, 92% of the extract was recovered as dried residue.

6.3 Biological Activity Analysis

Based on a literature review and according to the teaching of the method of the present invention, the following categories of bioassay were chosen to assess biological activity of Saw Palmetto for BPH in vitro: anti-androgenic, anti-inflammatory, cyclooxygenase/lipoxygenase (CO/LO) inhibition, muscle contractility. From these categories, the specific assays studied were as follows: 5-lipoxygenase assay, cyclooxygenase-1 assay, cyclooxygenase-2 assay (Panlabs, Wash.), and an androgen receptor assay developed at the Medical College of Georgia as described below.

6.3.1. Rat Prostatic Androgen Receptor Assay: Competitive Nuclear Receptor Ligand Binding Assay Against Dihydrotestosterone

6.3.1.1 Materials and Methods

Animals

Male rats were obtained at 60 days of age (300–350 g body weight) from Harlan (St. Louis, Mo.) and allowed to acclimate for 24 hours to an air-conditioned, light controlled room with a 12 hour light-dark cycle. Rats were fed with Purina chow and tap water, ad libitum.

All animals studies carried out were approved by the Medical College of Georgia Institutional Committee for the Care and Use of Animals in Research and Education in accordance with the guidelines of the National Institutes of Health and United States Department of Agriculture.

Steroid and Reagents

General chemicals (reagent grade), free fatty acids, fatty acid ethyl esters and radioinert steroids were obtained from Sigma Chemical Company (St. Louis, Mo.). $^3$H-dihydrotestosterone (5α-androstan-17β-ol-3-one; 60 Ci/mmol) was purchased from NEN Life Science Products (Boston, Mass.). 100% ethanol was used throughout for the preparations of all inhibitors and radioinert chemicals.

Androgen Receptor Binding

The animals were treated intraperitoneally with testosterone (400 μg/100 g body wt). After 1 hour, the animals were sacrificed by decapitation and the ventral prostates were rapidly removed and placed in ice-cold "homogenization buffer" (10 mM Tris-HCl, 1.5 mM $Na_2$EDTA, 0.5 mM dithiothreitol, 0.25 M sucrose, 1 mM phenylmethylsulfonylfluoride, pH 7.4 at 22° C.). The prostates were minced and homogenized on ice with a Polytron homogenizer (set at 4) using 10 second bursts alternated with a 30 second cooling period at a tissue-buffer ratio of 550 mg/ml. The homogenate was centrifuged at 800×g for 20 minutes at 4° C. The nuclear pellet was then resuspended in ice-cold "nuclear buffer" (10 mM Tris, 0.5 mM dithiothreitol, 0.25 M sucrose, 2.5 mM $MgCl_2$, pH 7.4 at 22° C., 550 mg tissue/ml). The resuspended pellet was homogenized on ice using a glass Dounce homogenizer until suspension became uniform.

Aliquots of the nuclear suspension obtained after rehomogenization of the nuclear pellets were dispensed into 12×75 mm glass test tubes containing 10 μl of $^3$H-dihydrotestosterone with or without 5 μl of various concentrations of inhibitors in a final volume of 1 ml. Non-specific binding was determined using radioinert dihydrotestosterone ($10^{-5}$ M) in place of the inhibitor. The test tubes were incubated for 20 hours at 15° C.

After an overnight incubation, 1 ml of ice-cold nuclear buffer was added followed by centrifugation at 800×g for 10 minutes at 4° C. The nuclear pellets were washed 3 times by resuspension in 1 ml of the same ice-cold nuclear buffer, with mixing and centrifugation as above. After discarding the final supernatant, 1 ml of 100% ethanol was added to each pellet and then vortexed. Test tubes were placed in a 30° C. water bath for 40 minutes, with vortexing every 10 minutes and a final centrifugation at 800 g for 10 minutes. The ethanol extracts were decanted into vials containing 4 ml of scintillation fluid (Ecoscint A), shaken and counted.

Compounds, extracts and fractions were screened at an initial concentration of $1 \times 10^{-5}$ and in some cases at $2 \times 10^{-5}$ M. If an activity of greater than 50% inhibition was observed at $2 \times 10^{-5}$ M or less, a full dose response curve was carried out. The results of this analysis are shown in the summary table for Saw Palmetto. $K_{50}$ displacements for lauric acid ester, linoleic acid ester and extract #3 are shown in FIGS. 4, 5 and 6 respectively.

The results, expressed as percent inhibition of $^3$H-Dihydrotestosterone binding, at two concentrations of putative active components, of the rat prostatic androgen receptor assay are below.

6.3.2. 5-Lipoxygenase Assay 5-lipoxygenase catalyzes the oxidative metabolism of arachidonic acid to 5-hydroxyeicosatetraenoic acid (5-HETE), the initial reaction in the biosynthetic pathway leading to the formation of the leukotrienes. The procedure was as follows. 5-lipoxygenase assays were run using a crude enzyme preparation from rat basophilic leukemia cells (RBL-1). Test compounds were pre-incubated with the enzyme for 5 minutes at room temperature and the reaction was initiated by addition of substrate (arachidonic acid). Following an 8 minute incubation at room temperature, the reaction was terminated by addition of citric acid, and levels of 5-HETE were determined by 5-HETE radioimmunoassay (RIA). Compounds are screened at 30 μM (Shimuzu et al., 1984, Proc. Natl. Acad. Sci. USA 81:689–693).

The following reference compounds were used for the inhibition of 5-lipoxygenase: reference compounds, ($IC_{50}$ (μM)): BW-755C, (6.6); nordihydroguaiaretic acid (NDGA), (0.26); phenidone, (30).

Compounds and fractions were screened at an initial concentration of $3 \times 10^{-5}$. If an activity of greater than 50% inhibition was observed at $3 \times 10^{-5}$, a full dose response curve was carried out. The results of this analysis are shown in the summary table for Saw Palmetto.

6.3.3. Cyclooxygenase-1 Assay

Cyclooxygenase-1 (from ram seminal vesicles), 125 units per assay tube, was pre-incubated with 1 mM GSH, 1 mM hydroquinone, 1.25 mM hemoglobin and test compound for 1 minute at 25° C. The reaction was initiated by addition of arachidonic acid (100 mM) and terminated after 20 minutes incubation at 37° C. by addition of trichloroacetic acid (TCA). Following centrifugal separation and addition of thiobarbiturate, cyclooxygenase activity was determined by reading absorbance at 530 nm (Evans et al., 1987, *Biochem. Pharamac.* 36:2035–2037; Boopathy and Balasubramanian, 1988, *J. Biochem.* 239:371–377).

The following reference compounds were used for the inhibition of cyclooxygenase 1: reference compounds, ($IC_{50}$ ($\mu M$)); aspirin, (240); indomethacin, (1.7).

Compounds and fractions were screened at an initial concentration of $3 \times 10^{-4}$ M. If an activity of greater than 50% inhibition was observed at $3 \times 10^{-4}$, a full dose response curve was carried out. The results of this analysis are shown in the summary table for Saw Palmetto.

6.3.4. Cyclooxygenase-2 Assay

Cyclooxygenase-2 (from sheep placenta), 80 units per assay tube, was pre-incubated with 1 mM GSH, 1 mM hydroquinone, 1.25 mM hemoglobin and test compound for 1 minute at 25° C. The reaction is initiated by addition of arachidonic acid (100 mM) and terminated after 20 minutes incubation at 37° C. by addition of TCA. Following centrifugal separation and addition of thiobarbiturate, cyclooxygenase activity is determined by reading absorbance at 530 nm (Boopathy and Balasubramanian, 1988; Evans et al. 1987; O'Sullivan et al., 1992, *Biochem. Biophy. Res. Commun.* 187:1123–1127).

The following reference compounds were used for the inhibition of cyclooxygenase-2: reference compounds, ($IC_{50}$ ($\mu M$)): aspirin, (660); indomethacin, (2.4).

6.3.5. 5-Alpha-reductase Assays

6.3.5.1 Preparation of Prostatic 5-Alpha-reductase from Rats

In a typical experiment, adult male Sprague-Dawley rats (10–20) are sacrificed by cervical dislocation. The prostates are removed and cleaned by removal of connective tissues. The tissues are maintained at 0–4° C. and suspended in a 3-fold volume of buffer A (20 mM sodium phosphate pH 6; 0.32 mM sucrose; and 0.1 mM dithiothreitol), cut, minced, and homogenized with a Polytron homogenizer. The homogenate is centrifuged at 10,000×g for 60 minutes and 10,000×g supernatant is centrifuged at 140,000×g for 60 minutes. The two pellets are combined and suspended in twice the pellet volume of buffer B (sodium phosphate 2 mM, pH 6.5; 2 M NaCl; digitonin 5 mg/ml; 0.1 mM EDTA, 40% glycerol and 1 mM dithiothreitol) at 0° C. for 60 minutes. The suspension is centrifuged at 150,000×g for 60 minutes and the supernatant containing solubilized 5-alpha-reductase after addition of 5 mM NADPH is estimated for its protein contents and stored at −70° C. as 5-alpha-reductase.

6.3.5.2 Preparation of Prostatic 5-Alpha-reductase from Humans

Human prostatic tissue is obtained from BPH patients undergoing surgical transvesical resections. The tissue is transported to the laboratory in ice cold saline within 60 minutes. The tissue samples are cleaned, chopped into 1–3 g pieces, and quick frozen in liquid nitrogen and stored at −70° C. BPH is confirmed by histological examination.

The prostatic tissues are thawed and cut with fine scissors (or pulverized at liquid $N_2$ temperature) and homogenized with one 30 second burst of sonicator at 4° C. in a 5-fold volume of buffer (100 mM Tris/HCl pH 7.4, 20% glycerol, 100 mM sodium citrate, 100 mM KCl, 1 mM EDTA and 15 mM β-mercaptoethanol). The homogenate is filtered through glass wool to remove cell debris and then centrifuged at 800 g for 10 minutes to provide a nuclear pellet. The supernatant is divided into 1 ml aliquots to be centrifuged at 120,000 g for 45 minutes to provide microsomal pellets containing 5-alpha-reductase which are stored at −70° C. or suspended in buffer B containing 0.25 mg/ml Lubrol PX or 0.5 mg/ml digitonin and passed through a 25 gauge syringe to make a homogenate which is centrifuged at 120,000 g for 45 minutes. The supernatant microsomal 5-alpha-reductase (estimate protein contents) is used in assays or stored in 40% glycerol at −20° C. without loss of activity.

6.3.5.3 Assay of 5-Alpha-reductase Activity

The 5-alpha-reductase assays are studied by following the reduction of radiolabelled [$^3$H] testosterone (T) to [3H] 5-α-dihydrotestosterone (DHT) at 37° C. Tubes (duplicates) with 1 ml Tris-HCl (pH 7.4) buffer containing 100 mM sodium citrate, 100 mM KCl, 20% (v/v) glycerol, 1 mM EDTA, 15 mM β-mercaptoethanol, 5 mM glucose-6-phosphate dehydrogenase and 1 $\mu$M-[$^3$H] testosterone, are preincubated at 37° C. for 15 minutes. The assays are started by the addition of 5–50 $\mu$l of 5-alpha-reductase (rat or human) in the presence or absence of inhibitors (SPB-extract from different sources and at different concentrations). Proscar™ (finasteride) is used as a positive control. The reaction is stopped by the addition of 1 ml diethylether containing 25 $\mu$g each of T, DHT, and 3-alpha-androstanediol. Each tube is vortexed, centrifuged, and the top ether layer separated. The ether is evaporated with a stream of nitrogen and the residue dissolved in 20 $\mu$l chloroform/methanol (2:1, v/v) and applied to thin layer plates (silica gel 60, E. Merck, 5748-7, Darmstadt, Germany). The plates are developed with chloroform/ethyl acetate (3:1, v/v), autoradiographed at −70° C. for 18 hours and radioactive zones (corresponding to T, DHT, and 3-alpha-androstanediol) cut and counted for radioactivity in a liquid scintillation counter. The method is used to calculate $K_m$ and $V_{max}$ values and percent inhibition of the conversion of T to DHT in presence of a SPB-extract at different concentrations.

The results of the bioassays presented below in the summary table 7.

SUMMARY TABLE 7

Saw Palmetto Extract - Biological Assay Results

| Component/Extract Fraction | Androgen Receptor | Cox1 | Cox2 | 5-Lipo |
|---|---|---|---|---|
| Extract #1 | Negative | Negative | Negative | Negative |
| Extract #2 | 30 nM* | Negative | Negative | Negative |
| Extract #3 | 3.5 uM | Negative | Negative | Negative |
| Extract #4 | Not tested | Negative | Negative | Negative |
| Extract #5 | Negative | Negative | Negative | Negative |
| Beta-Sitosterol | 60% @ 10 uM | Not tested | Not tested | Not tested |
| Lauric Acid | Negative | Negative | Negative | Negative |
| Linoleic Acid | Negative | Negative | Negative | Negative |
| Linolenic Acid | Negative | 233 uM | Negative | 12 uM |
| Myristic Acid | Negative | Negative | Negative | Negative |
| Oleic Acid | Negative | Negative | Negative | Negative |

SUMMARY TABLE 7-continued

Saw Palmetto Extract - Biological Assay Results

| Component/Extract Fraction | Androgen Receptor | Cox1 | Cox2 | 5-Lipo |
|---|---|---|---|---|
| Palmitic Acid | Negative | Negative | Negative | Negative |
| Lauric Ester | 130 nM | Negative | Negative | Negative |
| Linoleic Ester | 6 um | Negative | Negative | Negative |
| Linolenic Ester | Negative | Negative | Negative | Negative |
| Myristic Ester | Negative | Negative | Negative | Negative |
| Oleic Ester | Negative | Negative | Negative | Negative |
| Palmitic Ester | Negative | Negative | Negative | Negative |

A summary of the test results is presented in Table 8. Briefly, none of the commercially obtained extracts were active in the cyclooxygenase-1, cyclooxygenase-2 and 5-lipoxygenase assays and none of the 14 lots of commercially available saw palmetto berry extract products tested expressed α-adrenergic receptor activity. In addition, the 5α-reductase inhibitory activity of saw palmetto berry extract is reportedly approximately $\frac{1}{1,000}$ that of Finasteride (with $IC_{50}$ values in the 10–150 μM range, see Tables 3–5). For this reason, 5α-reductase was not examined as a potential site of saw palmetto berry extract activity. In contrast, one of three extracts tested showed significant inhibition of androgen binding in the nuclear androgen receptor assay. This suggested that the nuclear androgen receptor assay was appropriate for the biostandardization of saw palmetto extracts via the PharmaPrint Process.

An examination of saw palmetto berry extract components appeared to confirm that the nuclear androgen receptor was an appropriate bioassay, as two fatty acid ethyl esters (ethyl linoleate and ethyl laurate) and the phytosterol β-sitosterol expressed significant inhibitory activity on androgen receptor binding (see Table 8). Furthermore, the fatty alcohol phytol also appeared to be potent in this model system, inhibiting nuclear androgen receptor binding by 50% at 10 μM (not shown).

The nuclear androgen receptor assay identified a number of constituents of saw palmetto berry extract which are apparently bioactive, and which may, therefore, be of importance in defining a reproducibly manufactured saw palmetto berry extract.

TABLE 8

Saw Palmetto Commercial Off the Shelf Products and Constituents
$IC_{50}$ (μM) Values in Various Biological Assays

| Component/Product | Androgen Receptor | Cyclo-oxygenase-1 | Cyclo-oxygenase-2 | 5 Lipoxy-genase |
|---|---|---|---|---|
| Lauric Acid | * | * | * | * |
| Linoleic Acid | * | * | * | * |
| Linolenic Acid | * | 233 | * | 12 |
| Myristic Acid | * | * | * | * |
| Oleic Acid | * | * | * | * |
| Palmitic Acid | * | * | * | * |
| Ethyl Laurate | 0.13 | * | * | * |
| Ethyl Linoleate | 42 | * | * | * |
| Ethyl Linolenate | * | * | * | * |
| Ethyl Oleate | * | * | * | * |
| Ethyl Palmitate | * | * | * | * |
| β-Sitosterol | 2.4 | * | * | * |
| Commercial Product #1 | * | * | * | * |
| Commercial Product #2 | 2.2 | * | * | * |
| Commercial Product #3 | * | * | * | * |

* Negative (not active)

With fatty acid ethyl esters (specifically ethyl linoleate and ethyl laurate), β-sitosterol and phytol identified as constituents of saw palmetto berry extract likely to be related to clinical efficacy, 15 commercial samples of saw palmetto berry extract were examined by GC and GC-MS. FIGS. 6 and 7 show the variability of the individual free fatty acids (detected as their methyl esters) and the fatty acid ethyl esters, respectively, in these samples. These preparations represent a sample of the three major extraction production methods used commercially and were obtained from 6 different manufacturers.

Pivotal to this understanding is the selection of appropriate bioassays. Bioassay development and implementation are used for both product development and research purposes. A detailed discussion of this process is described herein. It is apparent from the data that the nuclear androgen receptor binding assay is the most viable bioassay available from our studies and therefore is to be used for release and stability testing.

The results indicate that the phytosterols (specifically β-sitosterol) and fatty acids, especially their ethyl esters, (specifically ethyl laurate, ethyl linoleate, and linolenic acid) play a significant role in the biological activity observed in extracts of saw palmetto. In addition, a fatty alcohol (specifically phytol) has significant activity in the androgen receptor binding assay, binding with an IC50 of 10 μM. The experiments were repeated six times. See Table 9 below.

TABLE 9

PHYTOL

| Concentration (M) | % Inh | % In | % In | % In | % In | % In | % In | Total | Mean | SE |
|---|---|---|---|---|---|---|---|---|---|---|
| 1.00E − 04 | 87.0 | 64. | 97. | 8.0 | 31. | 29. | 33. | 349.0 | 33.0 | 12.6 |
| 3.00E − 05 | 89.0 | 90. | 32. | 25. | 9.0 | 20. | 21. | 286.0 | 28.5 | 12.8 |
| 1.00E − 05 | 0.0 | 76. | 10. | 4.0 | 26. | 38. | 41. | 195.0 | 32.0 | 10.1 |
| 3.00E − 06 | 50.0 | 65. | 0.0 | 0.0 | 9.0 | 0.0 | 73. | 197.0 | 9.0 | 12.5 |
| 1.00E − 06 | 82.0 | 88. | 81. | 31. | 25. | 3.0 | 7.0 | 317.0 | 31.0 | 14.12 |
| 3.00E − 07 | 14.0 | 2.0 | 0.0 | | | | | 16.0 | 2.0 | 4.3 |

Analytical characterization is the second and equally important aspect of the PharmaPrint® Process as applied to saw palmetto berry extracts. These methods involve the use of capillary gas chromatography (GC) to examine the free fatty acid (FFA) and fatty acid ethyl ester (FAEE) components of the extract. A mixture of commercially available, high purity standards representing the FFA (as their fatty acid methyl esters, FAME No. 1 & FAME No.2, Restek, Inc.) or the FAEE (ethyl laurate, ethyl myristate, ethyl palmitate, ethyl linoleate, and ethyl linolenate, Nu-Check-Prep, Inc.) are effectively separated by capillary GC. The FFA and FAEE are measured in two separate assays in order to avoid transesterification side reactions involving the ethyl esters and to obtain the sensitivity required for the ethyl ester determinations. We also measure total fatty acids by complete hydrolysis and esterification to the methyl esters. The important phytosterol (β-sitosterol) and fatty alcohol (phytol) are measured in the same assays using HP5971A GC/MS System. All assays are described in detail above.

Table 10 presents the tabulation of the bioassay data for 16 commercial samples evaluated in the androgen receptor assay. An examination of the mean and standard deviation for collection of determination, indicates a large degree of variability in performance of this assay in the presence of the total extracts. This is in contrast to standards when presented as isolated pure compounds in the assay. The apparent extract assay inference could have a number of explanations. One explanation is the obvious potential for a oil extract to change the chemical nature of a membrane based system like the nuclear androgen receptor binding bioassay. At $10^{-5}$ M it is believed that this interference is less significant based on the ability to differentiate consistently between active extracts and less active or inactive extracts (compare SP379, 381, and 382 to SP383, 384, 393 and 394). We are using a qualitative evaluation greater than or equal to 20% inhibition at a concentration of $10^{-5}$ M. The experiments were repeated and the results summarized.

TABLE 10

| SAMPLE | CONC. | RESULTS | | | | | | MEAN | ST. DEV. |
|---|---|---|---|---|---|---|---|---|---|
| SP379 | $10^{-4}$ | 0 | 77 | 61 | 15 | 10 | 0 | 27.17 | 33.31 |
| | $10^{-5}$ | 3 | 2 | | | | | 2.50 | 0.71 |
| SP380 | $10^{-4}$ | 19 | 32 | | | | | 25.50 | 9.19 |
| | $10^{-5}$ | 45 | 0 | | | | | 22.50 | 31.82 |
| SP381 | $10^{-4}$ | 70 | 0 | 45 | 38 | 42 | 0 | 0 | 27.86 | 27.99 |
| | $10^{-5}$ | 0 | 4 | | | | | 2.00 | 2.83 |
| SP382 | $10^{-4}$ | 100 | 100 | 55 | 66 | 82 | 0 | 5 | 58.29 | 41.53 |
| | $10^{-5}$ | 12 | 0 | | | | | 6.00 | 8.49 |
| SP383 | $10^{-4}$ | 0 | 31 | | | | | 15.50 | 21.92 |
| | $10^{-5}$ | 63 | 35 | 0 | 28 | | | 31.50 | 25.88 |
| SP384 | $10^{-4}$ | 100 | 100 | | | | | 100.00 | 0.00 |
| | $10^{-5}$ | 60 | 37 | 47 | 6 | | | 37.50 | 23.01 |
| SP385 | $10^{-4}$ | 18 | 47 | | | | | 32.50 | 20.51 |
| | $10^{-5}$ | 38 | 0 | 36 | | | | 24.67 | 21.39 |
| SP386 | $10^{-4}$ | 52 | 50 | | | | | 51.00 | 1.41 |
| | $10^{-5}$ | 21 | 17 | | | | | 19.00 | 2.83 |
| SP387 | $10^{-4}$ | 0 | 14 | 0 | 100 | 98 | 46 | 46 | 43.43 | 42.48 |
| | $10^{-5}$ | 20 | 34 | | | | | 27.00 | 9.90 |
| SP388 | $10^{-4}$ | 0 | 69 | 0 | 9 | 100 | 5 | 30.50 | 43.09 |
| | $10^{-5}$ | 35 | 19 | | | | | 27.00 | 11.31 |
| SP389 | $10^{-4}$ | 1 | 0 | 65 | 25 | | | 22.75 | 30.45 |
| | $10^{-5}$ | 40 | 27 | | | | | 33.50 | 9.19 |
| SP391 | $10^{-4}$ | 30 | 9 | | | | | 19.50 | 14.85 |
| | $10^{-5}$ | 31 | 15 | | | | | 23.00 | 11.31 |
| SP393 | $10^{-4}$ | 14 | 3 | | | | | 8.50 | 7.78 |
| | $10^{-5}$ | 32 | 82 | 0 | 0 | 27 | 11 | 25.33 | 30.81 |
| | $10^{-6}$ | 27 | 41 | 49 | 84 | 1 | | 40.40 | 30.44 |
| | $10^{-7}$ | 68 | 20 | 35 | 23 | | | 36.50 | 21.98 |
| | $10^{-8}$ | 22 | 24 | 67 | 60 | 36 | 22 | 38.50 | 20.18 |
| | $10^{-9}$ | 0 | 13 | 100 | 10 | | | 30.75 | 46.50 |
| SP394 | $10^{-3}$ | 72 | 88 | | | | | 80.00 | 11.31 |
| | $10^{-4}$ | 100 | 100 | 0 | 20 | 16 | 0 | 39.33 | 47.69 |

TABLE 10-continued

| SAMPLE | CONC. | RESULTS | | | | MEAN | ST. DEV. |
|---|---|---|---|---|---|---|---|
| | $10^{-5}$ | 40 | 51 | 70 | 45 | 51.50 | 13.13 |
| | $10^{-6}$ | 0 | 19 | | | 9.50 | 13.44 |
| | $10^{-8}$ | 0 | 0 | | | 0.00 | 0.00 |

6.4 Chemical Analysis GC-MS, HPLC of Oleic, Lauric, Linoleic, Linolenic, Palmitic, Myristic Acids Both Free Fatty Acids and Ethyl Esters Several putative active compounds from the saw palmetto fruit have been identified (see Table 11). While a number of these identified constituents of saw palmetto berry are pharmacologically active, it remains to be demonstrated which, if any, of these compounds convey therapeutic activity in humans.

Analytical capillary GC Method: The GC system was a Varian GC/FID equipped with Star data handling software. Separations were made using 1 μl injection volumes injected onto a capillary column (Restek RTX-2330, 30 m column, 0.25 μm, 0.20 μmdf) and a temperature gradient system as follows: 55° C. for 1 min.; 7.5° C./min. to 260° C., hold for 5 min. The column flow rate was kept at 1.0 ml/min., with the injection split ratio 1:100. Injector and detector temperatures used were 260° C. There are many sources of standards for the Saw Palmetto assay, including Aldrich Chemical Co., Inc. (Milwaukee, Wis., USA).

FIG. 6 shows the value of the PharmaPrint® Process for saw palmetto, which displays the results of the capillary GC analysis of fifteen commercially available saw palmetto extracts. The relative variability among the extracts is striking. It is easy to see why "standardized" saw palmetto extracts which contain 85–95% fatty acids can vary significantly from lot to lot when considering either chemical constituents or biological potency. The general envelope of the ensemble as seen in FIG. 6 and 7 defines the fingerprint of saw palmetto FFAs and FAEEs. For the purpose of specifying the ensemble we look at the mean of each FFA across the fifteen extracts as seen in FIG. 8. The acceptable range is then defined by the 95% confidence limit of the ensemble or ±(1.8)SD. Other points to be made about the power of the PharmaPrint® Process has to do with the correlated use of biological data with analytical data.

Our data indicates that the FAEEs play a significant role in the biological activity observed in extracts of saw palmetto, as discussed earlier. FIG. 7 shows graphically that the FAEEs are enriched in the alcoholic extracts compared to the $CO_2$ or hexane extracts. This conclusion is consistent with the biological data presented in Table 8. There is very good correlation of the apparent biological activity in the nuclear androgen receptor binding assay and the level of FAEES. The abbreviated scheme utilizes the fact that, as described above, the ethanol extracts are enriched in the FAEEs. The process, starts exclusively with an ethanol extract and uses Quality Control testing (derived from the PharmaPrint® Process) to maintain the putative active components and to maintain the chemical ensemble profile of the saw palmetto extracts marketed Europe and forming the basis of the present clinical database. Thus the acceptance of raw material, bulk drug substance, and final drug product is a function of both tests for the ensemble and the active components as elucidated by the PharmaPrint® Process.

In selecting manufacturing processes which would be likely to result in potent, reproducible saw palmetto berry extracts, the PharmaPrint® Process (specifically the nuclear androgen receptor assay and chemical analysis by GC and GC-MS) identified saw palmetto berry extracts rich in fatty acid ethyl esters as likely to be potent biologically. Furthermore, levels of β-sitosterol and phytol could be important to bioactivity as well. Obviously, specifications and stability testing would need to reflect these findings. Thus, manufacturing processes in which fatty acid ethyl esters, β-sitosterol and phytol are maintained within appropriate specifications appear most likely to result in potent saw palmetto berry extracts.

TABLE 11

Components of the Extract

| Component | Carbons | Kloss[1] % | Hatinguais et al.[2] (1981) * | Neuzil and Cousse[3] % Free | % Esterified | PPRT-321[4] % |
|---|---|---|---|---|---|---|
| Caproic acid | C6:0 | 4.2 | FA | — | — | 0.5–2.0 |
| Caprylic acid | C8:0 | 4.6 | FA, ME | — | — | 0.9–2.7 |
| Capric acid | C10:0 | 0.9 | FA, ME | trace | — | 0.8–3.2 |
| Lauric acid | C12:0 | 30.7 | FA, ME | 20.3 | 20.1 | 16–38 |
| Myristic acid | C14:0 | 10 | FA | 15.2 | 12.7 | 6.5–15 |
| Palmitic acid | C16:0 | 7.3 | FA, ME | 11.5 | 10.2 | 4.0–8.8 |
| Stearic acid | C18:0 | — | FA, ME | 1.5 | 1.6 | 0.4–1.2 |
| Oleic acid | C18:1 | 42.4 | FA, ME | 46.1 | 42.3 | 9.0–24 |
| Linoleic acid | C18:2 | — | — | 1.6 | 2.4 | 0.7–3.4 |
| Linolenic acid | C18:3 | — | — | 2.5 | 1.4 | 0.2–0.7 |
| Ethyl Esters | | | | | | |
| Caprylate | | — | present | | | — |
| Caprate | | — | present | | | — |
| Laurate | | — | present | | | ≧2.2 |
| Myristate | | — | — | | | ≧0.8 |
| Palmitate | | — | present | | | ≧0.2 |
| Stearate | | — | present | | | — |

TABLE 11-continued

Components of the Extract

| Component | Carbons | Kloss[1] % | Hatinguais et al.[2] (1981) * | Neuzil and Cousse[3] % Free | Neuzil and Cousse[3] % Esterified | PPRT-321[4] % |
|---|---|---|---|---|---|---|
| Oleate | — | — | present | | | ≧1.5 |
| Linoleate | — | — | — | | | ≧0.1 |
| Linolenate | — | — | — | | | ≧0.02 |
| Unspecified | C24 + | — | — | 2–3% | 2–3% | — |

[1] From Neuzil and Cousse (1993a) (Item 8.7, Ref 11)
[2] Item 7, Ref 1
[3] Item 8.7, Ref 11
[4] Specifications for PPRT-321, included in Item 7.2.1
* FA = free fatty acid, ME = methyl ester

TABLE 12

Components of the Extract

| Component | Carbons | Kloss % | Hatinguais et al. (1981) | Neuzil and Cousse % Free | Neuzil and Cousse % Esterified | PPRT-321 % |
|---|---|---|---|---|---|---|
| β-sitosterol (24-β-ethyl cholesterol, 22, 23- | | 0.019 | present | present | | 0.1–0.5 |
| glucosides | | 0.028 | — | | | — |
| esters | | — | | | | — |
| ester glucodises | | — | | | | — |
| campesterol (24-β-methyl | | — | present | | | — |
| stigmasteroid | | — | present | | | — |
| farnesol | C15 | — | — | in hexane extract | | — |
| phytol | C20 | — | — | in hexane extract | | 0.01–0.15 |
| geranylgeraniol | C20 | — | — | in hexane extract | | — |
| anthranilic acid | | — | | in aqueous fraction | | — |
| anti-inflammatory polysaccharidic acid | | — | | in aqueous fraction | | — |
| flavonoids | | — | | in alcoholic | | — |
| rutin | | — | | in alcoholic | | — |
| isoquercitin | | — | | in alcoholic | | — |
| campferol-3-O-glucoside | | — | | in alcoholic | | — |
| apigenin-7-O-glucoside | | — | — | in alcoholic | | — |

Several commercially available Saw Palmetto products were analyzed for the following esters: methyl palmitate, methyl stearate, methyl oleate, methyl linoleate, ethyl laurate, methyl linolenate, ethyl myristate, methyl caproate, ethyl palmitate, methyl caprylate, methyl caprate, ethyl oleate, methyl laurate, ethyl linolenate, methyl myristate and ethyl linolineate. Results are in the table below (Table 13).

TABLE 13

| Saw Palmetto: | % w/w C71548#1 | C71548#2 | C71548#3 | C71548#4 | C71548#5 |
|---|---|---|---|---|---|
| methyl palmitate | 0.004 | 0 | 0.276 | 0.019 | 0.304 |
| methyl stearate | 0.249 | 0 | 0.728 | 0.049 | 0.714 |
| methyl oleate | 0.462 | 0.058 | 0.875 | 0.078 | 1.069 |
| methyl linoleate | 5.418 | 0.67 | 9.911 | 0.956 | 13.401 |
| methyl linolenate | 2.184 | 0.285 | 4.243 | 0.453 | 5.448 |
| methyl caproate | 2.225 | 1.14 | 3.24 | 0.552 | 3.059 |

TABLE 13-continued

| Saw Palmetto: | % w/w C71548#1 | C71548#2 | C71548#3 | C71548#4 | C71548#5 |
|---|---|---|---|---|---|
| methyl caprylate | 0.332 | 0.297 | 0.57 | 0.59 | 0.608 |
| methyl caprate | 0 | 3.276 | 13.871 | 1.102 | 11.67 |
| methyl laurate | 1.805 | 7.291 | 3.527 | 0.249 | 2.916 |
| methyl myristate | 0.121 | 0.815 | 0.191 | 0.011 | 0.269 |
| ethyl laurate | 0 | 0 | 0.036 | 0 | 0.004 |
| ethyl myristate | 0 | 0 | 0.019 | 0.002 | 0.004 |
| ethyl palmitate | 0.23 | 0.001 | 0.017 | 0.004 | 0.138 |
| ethyl oleate | 0 | 0 | 0.069 | 0.002 | 0 |
| ethyl linoleate | 0.002 | 0 | 0.115 | 0.01 | 0 |
| ethyl linolineate | 0 | 0 | 0.002 | 0 | 0.003 |
| Totals: | 13.028 | 13.833 | 37.414 | 4.058 | 39.303 |

6.4.1 Extraction Process

*Serenoa repens* dried fruits are ground and extracted with ethanol. The extract is then cooled and refiltered prior to final product Quality Control analysis and subsequent release. Specifications are presented below (Table 14).

TABLE 14

| *Serenoa repens* Purified Alcoholic Extract | |
|---|---|
| Quality | Specification |
| Total Fatty Acids | 85–95% |
| Total Fatty Alcohols | 0.01–0.15% |
| Total Sterols | 0.25–0.5% |
| β-Sitosterol | 0.15–0.35% |

Composition of Administered Product

Saw palmetto berry extract Raw Material provided by Indena met the specifications.

Additional manufacturing steps have been undertaken to bring the composition into specifications defined by the PharmaPrint Process and to ensure and document consistency of batch-to-batch biological potency and chemical composition. The composition of a representative batch is provided in Table 15.

TABLE 15

| Chemical Composition of Bulk Drug Substance | |
|---|---|
| CHARACTERISTIC | VALUE |
| Biopotency | >20% Inhibition @ $10^{-5}$M |
| Total Fatty Acids | 99.6% |
| Free Fatty Acids: | 67% |
| Ethyl Esters of: | 22% |
| Phytol | 0.1% w/w |
| β-Sitosterol | 0.15% w/w |

Table 16 and Table 17 summarize the testing performed on the starting Raw Material and Bulk Drug Substance (BDS).

TABLE 16

| Testing Result - Incoming Raw Material | | |
|---|---|---|
| CHARACTERISTIC | SPECIFICATIONS | VALUE |
| Total Fatty Acids | 80% w/w | |
| Free Fatty Acids: | | |
| Caproic acid | 0.5–2.0% w/w | 1.5% |
| Caprylic acid | 0.9–2.7% w/w | 1.6% |
| Capric acid | 0.8–3.2% w/w | 1.5% |
| Lauric acid | 16–38% w/w | 25% |
| Myristic acid | 6.5–15% w/w | 10% |
| Palmitic acid | 4.0–8.8% w/w | 6.0% |
| Stearic acid | 0.4–1.2% w/w | 0.6% |
| Oleic acid | 9.0–24% w/w | 16% |
| Linoleic acid | 0.7–3.4% w/w | 1.5% |
| Linolenic acid | 0.2–0.7% w/w | 0.4% |
| Ethyl Esters of: | | |
| Lauric acid | 2.2% w/w | 5.4% |
| Linoleic acid | 0.1% w/w | 0.3% |
| Myristic acid | 0.8% w/w | 2.3% |
| Palmitic acid | 0.2% w/w | 1.4% |
| Oleic acid | 1.5% w/w | 4.4% |
| Linolenic acid | 0.02% w/w | 0.12% |
| β-Sitosterol | 0.1–0.5% w/w | 0.16% w/w |
| Phytol | 0.01–0.15% w/w | 0.09% w/w |

TABLE 17

| Testing Results | | |
|---|---|---|
| CHARACTERISTIC | SPECIFICATIONS | VALUE |
| Total Fatty | 80% w/w | 106% |
| Free Fatty | | |
| Caproic acid | 0.5–2.0% w/w | 1.5% |
| Caprylic acid | 0.9–2.7% w/w | 1.6% |
| Capric acid | 0.8–3.2% w/w | 1.6% |
| Lauric acid | 16–38% w/w | 26% |
| Myristic acid | 6.5–15% w/w | 11% |
| Palmitic acid | 4.0–8.8% w/w | 6.2% |
| Stearic acid | 0.4–1.2% w/w | 0.6% |
| Oleic acid | 9.0–24% w/w | 16% |
| Linoleic acid | 0.7–3.4% w/w | 1.5% |
| Linolenic acid | 0.2–0.7% w/w | 0.4% |
| Ethyl Esters | | |
| Lauric acid | 2.2% w/w | 6.7% |
| Linoleic acid | 0.1% w/w | 0.4% |
| Myristic acid | 0.9% w/w | 2.7% |
| Palmitic acid | 0.3% w/w | 1.5% |

TABLE 17-continued

Testing Results

| CHARACTERISTIC | SPECIFICATIONS | VALUE |
|---|---|---|
| Oleic acid | 1.6% w/w | 4.7% |
| Linolenic acid | 0.02% w/w | 0.15% |
| Biopotency | | 41% Inhibition @$10^{-5}$M |

Analytical Analysis of Saw Palmetto Capsules

The determination of the concentration of free fatty acids and ethyl esters, as well as total fatty acids in saw palmetto capsules was carried out by gas chromatography using the methods described above. The total fatty acid content was determined similarly. The results of the fatty acid analyses are reported in Table 18 through 21.

Results:

TABLE 18

Concentration Free Fatty Acids and Ethyl Esters Lot 703433:

| Fatty Acid | 703433A % w/w | Concentration mg/cap | 703433B % w/w | Concentration mg/cap |
|---|---|---|---|---|
| Methyl Caproate | 0.13 | 0.78 | 0.29 | 1.75 |
| Methyl Caprylate | 0.24 | 1.42 | 0.29 | 1.72 |
| Methyl Caprate | 0.28 | 1.66 | 0.45 | 2.68 |
| Methyl Laurate | 2.48 | 14.91 | 3.88 | 23.33 |
| Ethyl Laurate | 0.11 | 0.67 | | |
| Methyl Myristate | 1.01 | 6.10 | 1.56 | 9.36 |
| Ethyl Myristate | 0.05 | 0.29 | | |
| Methyl Palmitate | 1.29 | 7.75 | 1.91 | 11.51 |
| Ethyl Palmitate | 0.05 | 0.28 | | |
| Methyl Stearate | 1.18 | 7.10 | 1.61 | 9.69 |
| Methyl Oleate | 3.46 | 20.80 | 5.18 | 31.20 |
| Ethyl Oleate | 0.16 | 0.94 | | |
| Methyl Linoleate | 0.45 | 2.70 | 0.66 | 3.98 |
| Ethyl Linoleate | 0.02 | 0.10 | | |
| Methyl Linolenate | 0.01 | 0.08 | 0.10 | 0.58 |
| Ethyl Linolenate | ND | ND | | |
| Sum of Free Fatty Acids and Ethyl Esters | 10.9% w/w | 65.6 mg/cap | 15.9% w/w | 95.8 mg/cap |

TABLE 19

Concentration Free Fatty Acids and Ethyl Esters Lot 040725:

| Fatty Acid | 040725A % w/w | Concentration mg/cap | 040725B % w/w | Concentration mg/cap |
|---|---|---|---|---|
| Methyl Caproate | 0.23 | 0.60 | 0.20 | 0.52 |
| Methyl Caprylate | 0.47 | 1.21 | 1.12 | 2.87 |
| Methyl Caprate | 0.43 | 1.11 | 0.93 | 2.37 |
| Methyl Laurate | 7.45 | 19.07 | 12.61 | 32.26 |
| Ethyl Laurate | 1.60 | 4.11 | | |
| Methyl Myristate | 3.39 | 8.67 | 5.88 | 15.04 |
| Ethyl Myristate | 0.76 | 1.95 | | |
| Methyl Palmitate | 2.63 | 6.74 | 9.95 | 25.46 |
| Ethyl Palmitate | 0.53 | 1.34 | | |
| Methyl Stearate | 0.35 | 0.88 | 2.76 | 7.05 |
| Methyl Oleate | 7.77 | 19.87 | 23.89 | 61.13 |
| Ethyl Oleate | 1.44 | 3.68 | | |
| Methyl Linoleate | 1.30 | 3.32 | 25.85 | 66.13 |
| Ethyl Linoleate | 0.12 | 0.30 | | |
| Methyl Linolenate | 0.02 | 0.05 | 3.05 | 7.79 |
| Ethyl Linolenate | 0.05 | 0.12 | | |
| Sum of Free Fatty Acids and Ethyl Esters | 28.5% w/w | 73.0 mg/cap | 86.2% w/w | 220.6 mg/cap |

TABLE 20

Concentration Free Fatty Acids and Ethyl Esters Lot 610002:

| Fatty Acid | 610002A % w/w | Concentration mg/cap | 610002B % w/w | Concentration mg/cap |
|---|---|---|---|---|
| Methyl Caproate | 0.30 | 0.37 | 0.50 | 0.61 |
| Methyl Caprylate | 0.82 | 1.00 | 1.65 | 2.01 |
| Methyl Caprate | 0.78 | 0.94 | 1.49 | 1.81 |
| Methyl Laurate | 14.26 | 17.35 | 22.36 | 27.21 |
| Ethyl Laurate | 6.89 | 8.38 | | |
| Methyl Myristate | 7.12 | 8.66 | 11.19 | 13.61 |
| Ethyl Myristate | 3.41 | 4.15 | | |
| Methyl Palmitate | 5.54 | 6.74 | 9.55 | 11.62 |
| Ethyl Palmitate | 2.41 | 2.93 | | |
| Methyl Stearate | 0.61 | 0.75 | 1.17 | 1.43 |
| Methyl Oleate | 19.24 | 23.41 | 35.60 | 43.31 |
| Ethyl Oleate | 7.64 | 9.29 | | |
| Methyl Linoleate | 0.87 | 1.05 | 1.82 | 2.22 |
| Ethyl Linoleate | 0.30 | 0.37 | | |
| Methyl Linolenate | 0.45 | 0.55 | .88 | 1.06 |
| Ethyl Linolenate | 0.21 | 0.25 | | |
| Sum of Free Fatty Acids and Ethyl Esters | 70.8 % w/w | 86.1 mg/capsule | 86.2% w/w | 104.9 mg/capsule |

TABLE 21

Concentration Free Fatty Acids and Ethyl Esters Lot HD11929:

| Fatty Acid | HD11929A % w/w | Concentration mg/cap | HD11929B % w/w | Concentration mg/cap |
|---|---|---|---|---|
| Methyl Caproate | 0.07 | 0.34 | 0.12 | 0.54 |
| Methyl Caprylate | 0.05 | 0.25 | 0.26 | 1.23 |
| Methyl Caprate | 0.08 | 0.39 | 0.33 | 1.53 |
| Methyl Laurate | 1.37 | 6.38 | 4.15 | 19.32 |
| Ethyl Laurate | 0.13 | 0.61 | | |
| Methyl Myristate | 0.65 | 3.03 | 1.81 | 8.45 |
| Ethyl Myristate | 0.07 | 0.31 | | |
| Methyl Palmitate | 0.73 | 3.40 | 1.82 | 8.49 |
| Ethyl Palmitate | 0.05 | 0.25 | | |
| Methyl Stearate | 0.70 | 3.24 | 0.97 | 4.52 |
| Methyl Oleate | 1.73 | 8.06 | 5.76 | 26.83 |
| Ethyl Oleate | 0.11 | 0.50 | | |
| Methyl Linoleate | 0.20 | 0.95 | 0.68 | 3.18 |
| Ethyl Linoleate | ND | ND | | |
| Methyl Linolenate | 0.05 | 0.22 | 0.14 | 0.65 |
| Ethyl Linolenate | ND | ND | | |
| Sum of Free Fatty Acids and Ethyl Esters | 6.0% w/w | 27.9 mg/cap | 16.0% w/w | 74.8 mg/cap |

TABLE 22

Concentration Free Fatty Acids and Ethyl Esters Lot 6PX008:

| Fatty Acid | 6PX008A % w/w | Concentration mg/cap | 6PX008B % w/w | Concentration mg/cap |
|---|---|---|---|---|
| Methyl Caproate | 0.23 | 0.72 | 0.22 | 0.67 |
| Methyl Caprylate | 0.60 | 1.85 | 0.83 | 2.53 |
| Methyl Caprate | 0.76 | 2.34 | 1.11 | 3.41 |
| Methyl Laurate | 8.25 | 25.30 | 12.42 | 38.11 |
| Ethyl Laurate | 0.37 | 1.15 | | |
| Methyl Myristate | 3.27 | 10.03 | 5.20 | 15.96 |
| Ethyl Myristate | 0.16 | 0.48 | | |
| Methyl Palmitate | 2.75 | 8.45 | 8.46 | 25.96 |
| Ethyl Palmitate | 0.11 | 0.34 | | |
| Methyl Stearate | 0.49 | 1.51 | 1.99 | 6.11 |
| Methyl Oleate | 8.27 | 25.38 | 20.18 | 61.95 |
| Ethyl Oleate | 0.40 | 1.23 | | |
| Methyl Linoleate | 1.66 | 5.09 | 12.47 | 38.27 |
| Ethyl Linoleate | 0.06 | 0.18 | | |
| Methyl Linolenate | 0.22 | 0.68 | 0.89 | 2.72 |
| Ethyl Linolenate | 0.03 | 0.08 | | |
| Sum of Free Fatty Acids and Ethyl Esters | 27.6% w/w | 84.8 mg/cap | 63.8% w/w | 195.7 mg/cap |

TABLE 23

Concentration Free Fatty Acids and Ethyl Esters Lot 49529HX:

| Fatty Acid | 49529HXA % w/w | Concentration mg/cap | 49529HZB % w/w | Concentration mg/cap |
|---|---|---|---|---|
| Methyl Caproate | 0.07 | 0.29 | 0.06 | 0.26 |
| Methyl Caprylate | 0.12 | 0.53 | 0.07 | 0.30 |
| Methyl Caprate | 0.15 | 0.68 | 0.16 | 0.74 |
| Methyl Laurate | 1.78 | 8.00 | 2.01 | 9.03 |
| Ethyl Laurate | ND | ND | | |
| Methyl Myristate | 0.76 | 3.41 | 0.96 | 4.30 |
| Ethyl Myristate | ND | ND | | |
| Methyl Palmitate | 0.67 | 2.99 | 10.83 | 48.64 |
| Ethyl Palmitate | ND | ND | | |
| Methyl Stearate | 0.11 | 0.50 | 3.71 | 16.64 |
| Methyl Oleate | 1.94 | 8.71 | 18.87 | 84.75 |
| Ethyl Oleate | ND | ND | | |
| Methyl Linoleate | 0.53 | 2.39 | 44.51 | 199.85 |
| Ethyl Linoleate | ND | ND | | |
| Methyl Linolenate | 0.09 | 0.41 | 6.15 | 27.60 |
| Ethyl Linolenate | ND | ND | 87.3% w/w | |
| Sum of Free Fatty Acids and Ethyl Esters | 6.2% w/w | 27.9 mg/cap | | 392.1 mg/cap |

The determination of the concentration of free fatty acids and ethyl esters, as well as total fatty acids in saw palmetto capsules was carried out by gas chromatography according to the methods described above. The total fatty acid content was determined similarly. The results of the fatty acid analyses are reported in Table 22 through 27.

Results:

TABLE 24

Concentration Free Fatty Acids and Ethyl Esters Lot 703433:

| Fatty Acid | Concentration % w/w | Concentration mg/capsule |
|---|---|---|
| Methyl Caproate | 0.13 | 0.78 |
| Methyl Caprylate | 0.24 | 1.42 |
| Methyl Caprate | 0.28 | 1.66 |
| Methyl Laurate | 2.48 | 14.91 |
| Ethyl Laurate | 0.11 | 0.67 |
| Methyl Myristate | 1.01 | 6.10 |
| Ethyl Myristate | 0.05 | 0.29 |
| Methyl Palmitate | 1.29 | 7.75 |
| Ethyl Palmitate | 0.05 | 0.28 |
| Methyl Stearate | 1.18 | 7.10 |
| Methyl Oleate | 3.46 | 20.80 |
| Ethyl Oleate | 0.16 | 0.94 |
| Methyl Linoleate | 0.45 | 2.70 |
| Ethyl Linoleate | 0.02 | 0.10 |
| Methyl Linolenate | 0.01 | 0.08 |
| Ethyl Linolenate | ND | ND |
| Sum of Free Fatty Acids and Ethyl Esters | 10.9% w/w | 65.6 mg/capsule |

TABLE 25

Concentration Total Fatty Acids Lot 703433:

| Fatty Acid | Concentration % w/w | Concentration mg/capsule |
|---|---|---|
| Methyl Caproate | 0.29 | 1.75 |
| Methyl Caprylate | 0.29 | 1.72 |
| Methyl Caprate | 0.45 | 2.68 |
| Methyl Laurate | 3.88 | 23.33 |
| Methyl Myristate | 1.56 | 9.36 |
| Methyl Palmitate | 1.91 | 11.51 |
| Methyl Stearate | 1.61 | 9.69 |
| Methyl Oleate | 5.18 | 31.20 |
| Methyl Linoleate | 0.66 | 3.98 |
| Methyl Linolenate | 0.10 | 0.58 |
| Sum of Total Fatty Acids | 15.9% w/w | 95.8 mg/capsule |

TABLE 26

Concentration Free Fatty Acids and Ethyl Esters Lot 040725:

| Fatty Acid | Concentration % w/w | Concentration mg/capsule |
|---|---|---|
| Methyl Caproate | 0.23 | 0.60 |
| Methyl Caprylate | 0.47 | 1.21 |
| Methyl Caprate | 0.43 | 1.11 |
| Methyl Laurate | 7.45 | 19.07 |
| Ethyl Laurate | 1.60 | 4.11 |
| Methyl Myristate | 3.39 | 8.67 |
| Ethyl Myristate | 0.76 | 1.95 |
| Methyl Palmitate | 2.63 | 6.74 |
| Ethyl Palmitate | 0.53 | 1.34 |
| Methyl Stearate | 0.35 | 0.88 |
| Methyl Oleate | 7.77 | 19.87 |
| Ethyl Oleate | 1.44 | 3.68 |
| Methyl Linoleate | 1.30 | 3.32 |
| Ethyl Linoleate | 0.12 | 0.30 |
| Methyl Linolenate | 0.02 | 0.05 |
| Ethyl Linolenate | 0.05 | 0.12 |
| Sum of Free Fatty Acids and Ethyl Esters | 28.5% w/w | 73.0 mg/capsule |

TABLE 27

Concentration Total Fatty Acids Lot 040725:

| Fatty Acid | Concentration % w/w | Concentration mg/capsule |
|---|---|---|
| Methyl Caproate | 0.20 | 0.52 |
| Methyl Caprylate | 1.12 | 2.87 |
| Methyl Caprate | 0.93 | 2.37 |
| Methyl Laurate | 12.61 | 32.26 |
| Methyl Myristate | 5.88 | 15.04 |
| Methyl Palmitate | 9.95 | 25.46 |
| Methyl Stearate | 2.76 | 7.05 |
| Methyl Oleate | 23.89 | 61.13 |
| Methyl Linoleate | 25.85 | 66.13 |
| Methyl Linolenate | 3.05 | 7.79 |
| Sum of Total Fatty Acids | 86.2% w/w | 220.6 mg/capsule |

TABLE 28

Concentration Free Fatty Acids and Ethyl Esters Lot 610002:

| Fatty Acid | Concentration % w/w | Concentration mg/capsule |
|---|---|---|
| Methyl Caproate | 0.30 | 0.37 |
| Methyl Caprylate | 0.82 | 1.00 |
| Methyl Caprate | 0.78 | 0.94 |
| Methyl Laurate | 14.26 | 17.35 |
| Ethyl Laurate | 6.89 | 8.38 |
| Methyl Myristate | 7.12 | 8.66 |
| Ethyl Myristate | 3.41 | 4.15 |
| Methyl Palmitate | 5.54 | 6.74 |
| Ethyl Palmitate | 2.41 | 2.93 |
| Methyl Stearate | 0.61 | 0.75 |
| Methyl Oleate | 19.24 | 23.41 |
| Ethyl Oleate | 7.64 | 9.29 |
| Methyl Linoleate | 0.87 | 1.05 |
| Ethyl Linoleate | 0.30 | 0.37 |
| Methyl Linolenate | 0.45 | 0.55 |
| Ethyl Linolenate | 0.21 | 0.25 |
| Sum of Free Fatty Acids and Ethyl Esters | 70.8% w/w | 86.1 mg/capsule |

TABLE 29

Concentration Total Fatty Acids Lot 610002:

| Fatty Acid | Concentration % w/w | Concentration mg/capsule |
|---|---|---|
| Methyl Caproate | 0.50 | 0.61 |
| Methyl Caprylate | 1.65 | 2.01 |
| Methyl Caprate | 1.49 | 1.81 |
| Methyl Laurate | 22.36 | 27.21 |
| Methyl Myristate | 11.19 | 13.61 |
| Methyl Palmitate | 9.55 | 11.62 |
| Methyl Stearate | 1.17 | 1.43 |
| Methyl Oleate | 35.60 | 43.31 |
| Methyl Linoleate | 1.82 | 2.22 |
| Methyl Linolenate | 0.88 | 1.06 |
| Sum of Total Fatty Acids | 86.2% w/w | 104.9 mg/capsule |

TABLE 30

Concentration Free Fatty Acids and Ethyl Esters Lot HD11929:

| Fatty Acid | Concentration % w/w | Concentration mg/capsule |
|---|---|---|
| Methyl Caproate | 0.07 | 0.34 |
| Methyl Caprylate | 0.05 | 0.25 |
| Methyl Caprate | 0.08 | 0.39 |
| Methyl Laurate | 1.37 | 6.38 |
| Ethyl Laurate | 0.13 | 0.61 |
| Methyl Myristate | 0.65 | 3.03 |
| Ethyl Myristate | 0.07 | 0.31 |
| Methyl Palmitate | 0.73 | 3.40 |
| Ethyl Palmitate | 0.05 | 0.25 |
| Methyl Stearate | 0.70 | 3.24 |
| Methyl Oleate | 1.73 | 8.06 |
| Ethyl Oleate | 0.11 | 0.50 |
| Methyl Linoleate | 0.20 | 0.95 |
| Ethyl Linoleate | ND | ND |
| Methyl Linolenate | 0.05 | 0.22 |
| Ethyl Linolenate | ND | ND |
| Sum of Free Fatty Acids and Ethyl Esters | 6.0% w/w | 27.9 mg/capsule |

TABLE 31

Concentration Total Fatty Acids Lot HD11929:

| Fatty Acid | Concentration % w/w | Concentration mg/capsule |
|---|---|---|
| Methyl Caproate | 0.12 | 0.54 |
| Methyl Caprylate | 0.26 | 1.23 |
| Methyl Caprate | 0.33 | 1.53 |
| Methyl Laurate | 4.15 | 19.32 |
| Methyl Myristate | 1.81 | 8.45 |
| Methyl Palmitate | 1.82 | 8.49 |
| Methyl Stearate | 0.97 | 4.52 |
| Methyl Oleate | 5.76 | 26.83 |
| Methyl Linoleate | 0.68 | 3.18 |
| Methyl Linolenate | 0.14 | 0.65 |
| Sum of Total Fatty Acids | 16.0% w/w | 74.8 mg/capsule |

TABLE 32

Concentration Free Fatty Acids and Ethyl Esters Lot 6PX008:

| Fatty Acid | Concentration % w/w | Concentration mg/capsule |
|---|---|---|
| Methyl Caproate | 0.23 | 0.72 |
| Methyl Caprylate | 0.60 | 1.85 |
| Methyl Caprate | 0.76 | 2.34 |
| Methyl Laurate | 8.25 | 25.30 |
| Ethyl Laurate | 0.37 | 1.15 |
| Methyl Myristate | 3.27 | 10.03 |
| Ethyl Myristate | 0.16 | 0.48 |
| Methyl Palmitate | 2.75 | 8.45 |
| Ethyl Palmitate | 0.11 | 0.34 |
| Methyl Stearate | 0.49 | 1.51 |
| Methyl Oleate | 8.27 | 25.38 |
| Ethyl Oleate | 0.40 | 1.23 |
| Methyl Linoleate | 1.66 | 5.09 |
| Ethyl Linoleate | 0.06 | 0.18 |
| Methyl Linolenate | 0.22 | 0.68 |
| Ethyl Linolenate | 0.03 | 0.08 |
| Sum of Free Fatty Acids and Ethyl Esters | 27.6% w/w | 84.8 mg/capsule |

TABLE 33

Concentration Total Fatty Acids Lot 6PX008:

| Fatty Acid | Concentration % w/w | Concentration mg/capsule |
|---|---|---|
| Methyl Caproate | 0.22 | 0.67 |
| Methyl Caprylate | 0.83 | 2.53 |
| Methyl Caprate | 1.11 | 3.41 |
| Methyl Laurate | 12.42 | 38.11 |
| Methyl Myristate | 5.20 | 15.96 |
| Methyl Palmitate | 8.46 | 25.96 |
| Methyl Stearate | 1.99 | 6.11 |
| Methyl Oleate | 20.18 | 61.95 |
| Methyl Linoleate | 12.47 | 38.27 |
| Methyl Linolenate | 0.89 | 2.72 |
| Sum of Total Fatty Acids | 63.8% w/w | 195.7 mg/capsule |

TABLE 34

Concentration Free Fatty Acids and Ethyl Esters Lot 49529HX:

| Fatty Acid | Concentration % w/w | Concentration mg/capsule |
|---|---|---|
| Methyl Caproate | 0.07 | 0.29 |
| Methyl Caprylate | 0.12 | 0.53 |
| Methyl Caprate | 0.15 | 0.68 |
| Methyl Laurate | 1.78 | 8.00 |
| Ethyl Laurate | ND | ND |
| Methyl Myristate | 0.76 | 3.41 |
| Ethyl Myristate | ND | ND |
| Methyl Palmitate | 0.67 | 2.99 |
| Ethyl Palmitate | ND | ND |
| Methyl Stearate | 0.11 | 0.50 |
| Methyl Oleate | 1.94 | 8.71 |
| Ethyl Oleate | ND | ND |
| Methyl Linoleate | 0.53 | 2.39 |
| Ethyl Linoleate | ND | ND |
| Methyl Linolenate | 0.09 | 0.41 |
| Ethyl Linolenate | ND | ND |
| Sum of Free Fatty Acids and Ethyl Esters | 6.2% w/w | 27.9 mg/capsule |

TABLE 35

Concentration Total Fatty Acids Lot 49529HX:

| Fatty Acid | Concentration % w/w | Concentration mg/capsule |
|---|---|---|
| Methyl Caproate | 0.06 | 0.26 |
| Methyl Caprylate | 0.07 | 0.30 |
| Methyl Caprate | 0.16 | 0.74 |
| Methyl Laurate | 2.01 | 9.03 |
| Methyl Myristate | 0.96 | 4.30 |
| Methyl Palmitate | 10.83 | 48.64 |
| Methyl Stearate | 3.71 | 16.64 |
| Methyl Oleate | 18.87 | 84.75 |
| Methyl Linoleate | 44.51 | 199.85 |
| Methyl Linolenate | 6.15 | 27.60 |
| Sum of Total Fatty Acids | 87.3% w/w | 392.1 mg/capsule |

TABLE 36

Incoming Raw Material Specifications

| CHARACTERISTIC | SPECIFICATIONS |
|---|---|
| Total Fatty Acids | 80% w/w |
| Free Fatty Acids: | |
| Caproic acid | 0.5–2.0% w/w |
| Caprylic acid | 0.9–2.7% w/w |
| Capric acid | 0.8–3.2% w/w |
| Lauric acid | 16–38% w/w |
| Myristic acid | 6.5–15% w/w |
| Palmitic acid | 4.0–8.8% w/w |
| Stearic acid | 0.4–1.2% w/w |
| Oleic acid | 9.0–24% w/w |
| Linoleic acid | 0.7–3.4% w/w |
| Linolenic acid | 0.2–0.7% w/w |
| Ethyl Esters of: | |
| Lauric acid | 2.2% w/w |
| Linoleic acid | 0.1% w/w |
| Myristic acid | 0.8% w/w |
| Palmitic acid | 0.2% w/w |
| Oleic acid | 1.5% w/w |
| Linolenic acid | 0.02% w/w |
| β-Sitosterol | 0.1–0.5% w/w |
| Phytol | 0.01–0.15% |

6.5 Contribution of the Individual Components to the Total Activity

Five commercially available extracts of Saw Palmetto were quantitatively analyzed to determine the amount of several fatty acids and fatty acid esters present in each extract. The results are depicted in FIG. 5. The figures shows the wide variability of each of the components present in the various extracts.

Each of the fatty acids and fatty acid esters, i.e., the components, of FIGS. 5–8 were analyzed to determine their activity in four bioassays relevant for the BPH clinical indication, see above. None of the components showed activity against COX-2. The activities, $IC_{50}$s, for purified components in the other three bioassays were as follows: linolenic acid (233 $\mu$M in COX-1, 12 $\mu$M in 5-LIPO); linoleic acid ethyl ester (6 $\mu$M in androgen receptor assay); lauric acid ethyl ester (130 nM in androgen receptor assay); and β-sitosterol (~10 $\mu$M in the androgen receptor assay). Because none of the extracts was active in the COX-1 and 5-LIPO assay, the androgen receptor assay was selected for the calculations shown below.

The contribution of each individual component to the observed total bioactivity is calculated using (i) the total bioactivity of the botanical extract, (ii) the amount of each component present in each extract and (iii) the $IC_{50}$s of each purified component. This calculation is exemplified below using commercial sample #2 and the androgen receptor assay. Sample #2 has a total extract $IC_{50}$ value for the androgen receptor of 2.2 $\mu$M (total bioactivity), assuming the average molecular weight of the components is 200. A capsule of sample #3 contains the following proportions of the ethyl esters of lauric acid (0.067 W/W %; 228 MW) and linoleic acid (1.5 W/W %; 308 MW). A calculation of the percent contribution of the androgen receptor bioactivity of lauric acid ethyl ester relative to the total extract bioactivity is made using the following formula: the extract $IC_{50}$ bioactivity (2.2 $\mu$M=2,200 nM; average MW <200>) is multiplied times the amount of lauric acid ethyl ester present (0.027% W/W) and then divided by the lauric acid ethyl ester observed $IC_{50}$ (130 nM) and multiplied by 100 and corrected for the molecular weight (2,200 nM×200 MW×0.067×100)/(130 nM×228 MWt)=99.5%]. The percent contribution of linoleic acid ethyl ester using the same formula is calculated as follows: (2.2 μM 35×200×0.004× 100)/(41.7×308)=0.01%. Thus, two of the components in combination, lauric acid ethyl ester and linoleic ethyl ester, account for 99% of the observed in vitro bioactivity in this assay and are defined as active components in the androgen receptor bioassay.

The combined bioactivity of the lauric and linoleic ethyl esters is used to define a bioactivity standard for acceptance or rejection of pharmaceutical grade compositions.

The bioactivity ranges are set to determine if a given botanical qualifies as a pharmaceutical grade botanical as follows: In one calculation, the requirements are set such that the active components must account for 25% of the bioactivity based on the active component standard described above. Given the bioactivity required (25% of the standard) and known bioactivity for the active component, the calculation is as follows: The weight percent of the active component multiplied by the minimal percentage of the biological activity required, e.g., (0.036% W/W×25%= 0.009% W/W) for lauric acid. Similarly, for linoleic acid this must account for 0.42%. Alternatively, the requirements are established such the combination of the two esters accounts for at least 25% of the observed bioactivity.

Requiring that each component account for 50% of the bioactivity, the sample must contain at least 0.018% W/W lauric acid ester or 0.84% linoleic acid ester.

Requiring that each component account for 70% of the bioactivity, the sample must contain at least 0.025% W/W lauric acid ester or 1.176% W/W linoleic acid ester.

Requiring that each component account for 80% of the bioactivity, the sample must contain at least 0.029% W/W lauric acid ester or 1.344% linoleic acid ester.

Using either combined lauric and linoleic ethyl esters or the individual esters bioactivities, we can set now clearly defined standards for acceptance or rejection for pharmaceutical grade compositions of each of the five commercial samples tested on the basis of % W/W of these esters. For the five commercial samples shown in FIG. 5, even using the least rigorous requirements, e.g. 25%, samples 1, 2, 4 and 5 are rejected as unsuitable for pharmaceutical grade drug compositions due to the levels of the two esters determined for each sample.

The invention described and claimed herein is not to be limited in scope by the specific embodiments herein disclosed since these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. Throughout this application various publications and patents are cited in parenthesis. Their contents are hereby incorporated by reference into the present application.

We claim:

1. A method for determining a standard bioactivity for a saw palmetto extract comprising:

obtaining a sample of alcoholic saw palmetto extract;

measuring a total bioactivity for the sample by determining an IC50 in an androgen receptor binding inhibition assay;

measuring the total fatty acid content of an aliquot of the whole sample;

fractionating the sample and collecting the individual fractions;

measuring the fatty acid content of each fraction;

identifying the fractions containing linoleic acid ethyl ester and lauric acid ethyl ester;

measuring a bioactivity for each of the fractions identified in the step above with an androgen receptor binding inhibition assay;

calculating the percent activity of each of the fractions for which androgen receptor binding inhibition has been assayed compared to the total bioactivity of the sample, wherein the molecular weight and amount of the individual fatty acids identified are incorporated into the calculating; and determining that if the total bioactivity of the sample is above a selected minimum standard amount, and if the total percent activity of the linoleic and lauric acid ethyl ester fractions is at least 25% of the total bioactivity, then the saw palmetto extract has a standard bioactivity.

* * * * *